US010546657B2

United States Patent
Leonhardt et al.

(10) Patent No.: US 10,546,657 B2
(45) Date of Patent: Jan. 28, 2020

(54) SYSTEMS, METHODS AND COMPUTER PROGRAM PRODUCTS FOR REDUCING THE RISK OF PERSONS HOUSED WITHIN A FACILITY BEING SEXUAL PREDATORS OR VICTIMS

(71) Applicant: CENTINAL GROUP, LLC, Macclesfield, NC (US)

(72) Inventors: Gary G. Leonhardt, Macclesfield, NC (US); Mark R. Cervi, Greenville, NC (US); Peter Romary, Greenville, NC (US)

(73) Assignee: CENTINAL GROUP, LLC, Macclesfield, NC (US)

( * ) Notice: Subject to any disclaimer, the term of this patent is extended or adjusted under 35 U.S.C. 154(b) by 1204 days.

(21) Appl. No.: 14/748,815

(22) Filed: Jun. 24, 2015

(65) Prior Publication Data
US 2016/0019362 A1 Jan. 21, 2016

Related U.S. Application Data

(60) Provisional application No. 62/026,976, filed on Jul. 21, 2014.

(51) Int. Cl.
*G16H 50/30* (2018.01)
*G06Q 50/26* (2012.01)

(52) U.S. Cl.
CPC ......... *G16H 50/30* (2018.01); *G06Q 50/265* (2013.01)

(58) Field of Classification Search
CPC ......... H04W 4/90; G06Q 10/10; G06Q 50/22; G06Q 10/08; G06Q 20/10; H04L 63/083; G07D 7/004; G07C 9/00007
See application file for complete search history.

(56) References Cited

U.S. PATENT DOCUMENTS 5,782,778 A 7/1998 De Briere et al.
6,470,319 B1 * 10/2002 Ryan ..................... G06Q 10/10
                                                        705/325

(Continued)

FOREIGN PATENT DOCUMENTS

CN 101697895 A 4/2010
CN 101697896 A 4/2010

(Continued)

*Primary Examiner* — Robert W Morgan
*Assistant Examiner* — Edward B Winston, III
(74) *Attorney, Agent, or Firm* — Myers Bigel, P.A.

(57) ABSTRACT

Methods, systems and computer program products are provided for reducing the risk of sexual assault in a facility. Objective, clinical, and subjective information is obtained about a person housed within the facility. The obtained information is converted into respective groups of variables and weighted coefficients are assigned to selected ones of the variables. The respective groups of variables are processed via an algorithm to derive a risk number for the person. The risk number represents a risk of the person being vulnerable to rape within the facility or a risk of the person being a sexual predator within the facility. One or more other persons within the facility are identified that may be a potential sexual victim of the person and/or that may be a potential sexual abuser of the person based upon the risk number and respective risk numbers of each of the one or more other persons.

27 Claims, 13 Drawing Sheets

(56) References Cited

U.S. PATENT DOCUMENTS

| | | | |
|---|---|---|---|
| 7,752,125 B1* | 7/2010 | Kothari | G06Q 20/10 705/38 |
| 7,857,452 B2 | 12/2010 | Martinez-Conde et al. | |
| 8,099,668 B2 | 1/2012 | Garbow et al. | |
| 8,441,353 B2 | 5/2013 | Williams, Sr. et al. | |
| 8,589,328 B1 | 11/2013 | Sharma | |
| 8,713,450 B2 | 4/2014 | Garbow et al. | |
| 8,725,672 B2 | 5/2014 | Rostampour et al. | |
| 9,491,277 B2* | 11/2016 | Vincent | H04W 4/90 |
| 2007/0048706 A1 | 3/2007 | Tan | |
| 2007/0266439 A1* | 11/2007 | Kraft | H04L 63/083 726/26 |
| 2008/0218335 A1* | 9/2008 | Attar | G06Q 10/08 340/539.13 |
| 2008/0282324 A1 | 11/2008 | Hoal | |
| 2009/0012419 A1 | 1/2009 | McKee | |
| 2009/0089417 A1 | 4/2009 | Giffin et al. | |
| 2009/0106734 A1 | 4/2009 | Riesen et al. | |
| 2012/0308971 A1 | 12/2012 | Shin et al. | |
| 2014/0006042 A1 | 1/2014 | Keefe et al. | |
| 2014/0263615 A1* | 9/2014 | Deangelo | G07D 7/004 235/375 |
| 2014/0365240 A1* | 12/2014 | Canton | G06Q 50/22 705/3 |
| 2016/0055692 A1* | 2/2016 | Trani | G07C 9/00007 340/5.61 |
| 2016/0253672 A1* | 9/2016 | Hunter | G06Q 20/4016 705/39 |

FOREIGN PATENT DOCUMENTS

| | | |
|---|---|---|
| CN | 101697900 A | 4/2010 |
| KR | 101282790 B1 | 7/2013 |

* cited by examiner

220

1) Level of emotional or cognitive delay or appears 'Street smart' (language and executive skills)

2) Inmate's perception of vulnerability or feels at home in jail

3) Assertive vs. passive (Self confidence)

Sexuality related questions:

1) Inmate's declared sexual preferences

2) Identifies with children

3) Professes sexual deviancy

4) Professes sexual aggression

5) Abuse experiences

222

1) Tell me about yourself....where are you from and how did you end up coming here?

2) Do you have any concerns about your safety here? Is there anyone or type of person in particular that you would be fearful of while incarcerated?

3) What might you do if somebody were to try to attack you?

Now I'm going to ask you some questions that you might find awkward or embarrassing, but I won't know these things unless I ask.

1) Please tell me what you consider your sexual preference....would you consider yourself to be heterosexual, gay, bisexual or other?

2) Do you ever find yourself sexually attracted to really young people?

3) How many times have you ever been in a situation of a sexual nature that others would find odd or maybe even taboo to the average person?

4) When you have sex, do you find yourself being aggressive or hurtful to the other person?

5) How many times were you ever sexually abused in the past?

1) Tell me about yourself....where are you from and how did you end up coming here?
Delayed — Functional 2) Do you have any concerns about your safety here? Is there anyone or type of person in particular that you would be fearful of while incarcerated?
No concerns — Very Worried 3) What might you do if somebody were to try to attack you?
Feels helpless — Anything required

224

1) Please tell me what you consider your sexual preference...would you consider yourself to be heterosexual, gay, bisexual or other?
Gay — Not Gay 2) Do you ever find yourself sexually attracted to really young people?
Always — Never 3) How many times have you ever been in a situation of a sexual nature that others would find odd or maybe even taboo to the average person?
Never — Many Times 4) When you have sex, do you find yourself being aggressive or hurtful to the other person?
Never — Always 5) How many times were you ever sexually abused in the past?
Never — Greater than 10 times

SYSTEMS, METHODS AND COMPUTER PROGRAM PRODUCTS FOR REDUCING THE RISK OF PERSONS HOUSED WITHIN A FACILITY BEING SEXUAL PREDATORS OR VICTIMS

RELATED APPLICATION

This application claims the benefit of and priority to U.S. Provisional Patent Application No. 62/026,976 filed Jul. 21, 2014, the disclosure of which is incorporated herein by reference as if set forth in its entirety.

RESERVATION OF COPYRIGHT

A portion of the disclosure of this patent document contains material to which a claim of copyright protection is made. The copyright owner has no objection to the facsimile reproduction by anyone of the patent document or the patent disclosure, as it appears in the Patent and Trademark Office patent file or records, but reserves all other rights whatsoever.

FIELD OF THE INVENTION

The present invention relates generally to controlled facilities and, more particularly, to screening individuals within controlled facilities.

BACKGROUND

Prison rape refers to the rape of inmates in prison by other inmates or prison staff. The Prison Rape Elimination Act of 2003 ("PREA") was the first United States federal law passed specifically dealing with the sexual assault of prisoners. PREA requires the Bureau of Justice Statistics (BJS) to carry out a comprehensive statistical review and analysis of the incidence and effects of prison rape for each calendar year. PREA applies to all correctional facilities, including prisons, jails, juvenile facilities, military and Indian facilities, and Immigration and Customs Enforcement (ICE) facilities. BJS's review must include, but is not limited to, the identification of common characteristics of both victims and perpetrators of prison rape, and prisons and prison systems with a high incidence of prison rape. The annual review and analysis must satisfy the following requirements: 1) be based on a random sample, or other scientifically appropriate sample, of not less than 10% of all federal, state, and county prisons, and a representative sample of municipal prisons; and include at least one prison from each state; 2) use surveys and other statistical studies of current and former inmates from a representative sample of federal, state, county, and municipal prisons; and ensure the confidentiality of each survey participant; 3) provide a list of institutions in the sample, separated into each category and ranked according to the incidence of prison rape in each institution; and 4) provide a list of any prisons in the sample that did not cooperate with the survey.

Unfortunately, even after implementation of PREA, prison rape continues to be a concern and, due to the sensitive nature of violent victimization and potential reluctance to report sexual assault, the occurrence of prison rape continues to be underestimated. As such, there continues to be a need for ways of reducing the occurrence of prison rape.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, a method of reducing the risk of sexual assault in a facility (e.g., a correction facility), includes receiving objective information about a person (e.g., an inmate) housed in the facility from a first source, receiving clinical information about the person from a second source, and obtaining subjective information about the person via an observer of the person. The first source may include one or more sources of data (e.g., databases or other data storage systems), such as law enforcement databases, court system databases, and/or government databases, etc. Exemplary types of information obtained from the first source may include one or more of the following: age, race, marital status, number of previous incarcerations of the person, violent nature of charges against the person, previous convictions of the person for sex related crimes against a child or adult, whether the person is incarcerated strictly for immigration purposes, convictions of the person for physically aggressive sexual act(s), prior convictions of the person for other violent offenses, history of institutional violence and/or sexual offence(s) by the person, and gang affiliation.

The second source may include one or more sources of clinical data (e.g., databases or other data storage systems), such as healthcare provider databases. Exemplary types of information obtained from the second source may include physical information, psychiatric information, and/or medical information. The subjective information may include information about the person observed by the observer and/or information obtained from the person via one or more predetermined questions or series of questions asked by the observer.

The obtained objective, clinical and subjective information is converted into respective groups of one or more variables that can be processed by an algorithm. Weighted coefficients are assigned to selected ones of the one or more variables in the respective groups, and the respective groups of one or more variables are then processed via the algorithm to derive a risk number for the person. The risk number represents a risk of the person being vulnerable to rape within the facility or a risk of the person being a sexual predator within the facility. The risk number may then be communicated to one or more systems associated with the facility, such as monitoring systems, access control systems, etc.

In some embodiments, a color code may be assigned to the risk number of the person. The color code represents a risk of the person being vulnerable to rape or a risk of the person being a sexual predator. The color code can be used when displaying information about the person via a monitoring system of the facility.

In some embodiments, the method further comprises identifying one or more other persons within the facility that may be a potential sexual victim of the person and/or that may be a potential sexual abuser of the person based upon the risk number of the person and respective risk numbers of each of the one or more other persons. In addition, an identification of the one or more other persons that may be a potential sexual victim of the person and/or that may be a potential sexual abuser of the person is communicated to a monitoring system(s) of the facility.

In some embodiments, the method further comprises activating one or more devices within the facility to facilitate isolation of the person from the one or more other persons that may be a potential sexual victim of the person and/or that may be a potential sexual abuser of the person. Exemplary devices may include electronic monitoring devices worn by persons in the facility including, but not limited to, ankle bracelets, RFID devices, GPS devices, etc. In some embodiments, activating one or more devices within the facility to facilitate isolation of the person includes locking and/or unlocking one or more doors or barriers within the facility.

According to some embodiments of the present invention, a system for reducing the risk of sexual assault in a facility (e.g., a correctional facility) includes a data collection component that is configured to receive objective information about a respective person (e.g., an inmate) housed within the facility from a first source, receive clinical information about the person from a second source, and receive subjective information about the person from an observer of the person. The system further includes at least one processor that is configured to convert the objective, clinical and subjective information into respective groups of one or more variables and to assign weighted coefficients to selected ones of the one or more variables in the respective groups. The at least one processor then processes the respective groups of one or more variables via at least one algorithm to derive a risk number for the person, wherein the risk number represents a risk of the person being vulnerable to rape within the facility or a risk of the person being a sexual predator within the facility. The at least one processor may then communicate the risk number to one or more systems associated with the facility, such as monitoring systems, access control systems, etc.

In some embodiments, the at least one processor may assign a color code to the risk number of the person. The color code represents a risk of the person being vulnerable to rape or a risk of the person being a sexual predator. The color code can be used when displaying information about the person via a monitoring system of the facility.

The first source may include one or more sources of data (e.g., databases or other data storage systems), such as law enforcement databases, court system databases, and/or government databases. Exemplary types of information obtained from the first source may include one or more of the following: age, race, marital status, number of previous incarcerations of the person, violent nature of charges against the person, previous convictions of the person for sex related crimes against a child or adult, whether the person is incarcerated strictly for immigration purposes, convictions of the person for physically aggressive sexual act(s), prior convictions of the person for other violent offenses, history of institutional violence and/or sexual offence(s) by the person, and gang affiliation.

The second source may include one or more sources of clinical data (e.g., databases or other data storage systems), such as healthcare provider databases. Exemplary types of information obtained from the second source may include physical information, psychiatric information, and/or medical information. The subjective information may include information about the person observed by the observer and/or information obtained from the person via one or more predetermined questions or series of questions asked by the observer.

In some embodiments, the at least one processor is configured to identify one or more other persons within the facility that may be a potential sexual victim of the person and/or that may be a potential sexual abuser of the person based upon the risk number of the person and respective risk numbers of each of the one or more other persons. In addition, an identification of the one or more other persons that may be a potential sexual victim of the person and/or that may be a potential sexual abuser of the person is communicated to a monitoring system(s) of the facility.

In some embodiments, the at least one processor is configured to activate one or more devices within the facility to facilitate isolation of the person from the one or more other persons that may be a potential sexual victim of the person and/or that may be a potential sexual abuser of the person. Exemplary devices may include electronic monitoring devices worn by persons in the facility including, but not limited to, ankle bracelets, RFID devices, GPS devices, etc. In some embodiments, the at least one processor may be configured to lock and/or unlock one or more doors or barriers within the facility.

According to some embodiments of the present invention, a computer program product includes a non-transitory computer readable storage medium having encoded thereon instructions that, when executed on a processor, cause the processor to perform operations including receiving objective information about a person housed in the facility from a first source, receiving clinical information about the person from a second source, receiving subjective information about the person from an observer of the person, converting the objective, clinical and subjective information into respective groups of one or more variables that can be processed by an algorithm, and processing the respective groups of one or more variables via the algorithm to derive a risk number for the person. The risk number represents a risk of the person being vulnerable to rape within the facility or a risk of the person being a sexual predator within the facility.

The first source may include one or more sources of data (e.g., databases or other data storage systems), such as law enforcement databases, court system databases, and/or government databases. Exemplary types of information obtained from the first source may include one or more of the following: age, race, marital status, number of previous incarcerations of the person, violent nature of charges against the person, previous convictions of the person for sex related crimes against a child or adult, whether the person is incarcerated strictly for immigration purposes, convictions of the person for physically aggressive sexual act(s), prior convictions of the person for other violent offenses, history of institutional violence and/or sexual offence(s) by the person, and gang affiliation.

The second source may include one or more sources of clinical data (e.g., databases or other data storage systems), such as healthcare provider databases. Exemplary types of information obtained from the second source may include physical information, psychiatric information, and/or medical information. The subjective information may include information about the person observed by the observer and/or information obtained from the person via one or more predetermined questions or series of questions asked by the observer.

In some embodiments, the computer readable storage medium has encoded thereon instructions that, when executed on the processor, cause the processor to perform operations including identifying one or more other persons within the facility that may be a potential sexual victim of the person and/or that may be a potential sexual abuser of the person based upon the risk number of the person and respective risk numbers of each of the one or more other persons, and communicating an identification of the one or more other persons that may be a potential sexual victim of the person and/or that may be a potential sexual abuser of the person to a system of the facility, such as a monitoring system, access control system, etc.

In some embodiments, the computer readable storage medium has encoded thereon instructions that, when executed on the processor, cause the processor to perform operations including activating one or more devices within the facility to facilitate isolation of the person from the one or more other persons that may be a potential sexual victim of the person and/or that may be a potential sexual abuser of the person.

In some embodiments, the computer readable storage medium has encoded thereon instructions that, when executed on the processor, cause the processor to perform operations including communicating the risk number of the person to a monitoring system of the facility.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate some exemplary embodiments. The drawings and description together serve to fully explain the exemplary embodiments.

FIG. 4 illustrates a list of topics and associated questions that can be asked by an observer of an inmate to facilitate the determination of a risk number for the inmate, according to some embodiments of the present invention.

FIG. 5 illustrates the list of questions from FIG. 4 along with a scoring scale or gradient for each question or group of related questions.

FIG. 6 illustrates the list questions and respective scoring gradients of FIG. 5 after an observer has indicated scores for the various topics of FIG. 4.

DETAILED DESCRIPTION

Figure 1:
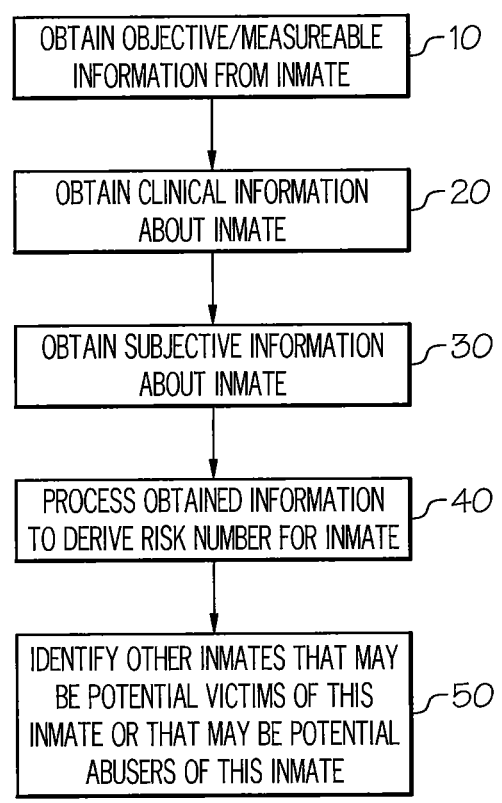
FIG. 1 is a flowchart of operations for predicting prison inmates who may be vulnerable to rape, and prison inmates who may be sexual predators, in accordance with some embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain components or features may be exaggerated for clarity, and broken lines may illustrate optional features or elements unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

As used herein, the term "and/or" includes any and all combinations of one or more of the associated listed items and may be abbreviated as "/".

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will also be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "about", as used herein with respect to a value or number, means that the value or number can vary by +/−20%, +/−10%, +/−5%, +/−1%, +/−0.5%, or even +/−0.1%.

The term "facility", as used herein, refers to an area delineated by a specific boundary, and may include both indoor areas and outdoor areas within the boundary. For example, a correctional institution, such as a prison, has a specific boundary and also typically includes both indoor areas and outdoor areas within the boundary.

The term "GUI control", as used herein, refers to graphical representations (e.g., application icons) and controls (e.g., buttons, scroll bars, etc.) that a user utilizes to interact with various GUIs. A GUI control performs one or more functions in response to activation by a user (e.g., mouse pointer and click, touching or tapping via a finger or stylus if a touch screen display is used, etc.).

The terms "rape", "abuse", and "sexual abuse", as used herein, are intended to be interchangeable.

The present invention may be embodied as systems, methods, and/or articles of manufacture (e.g., one or more computer program products) for predicting prison inmates who may be vulnerable to rape/sexual abuse, and prison inmates who may be sexual predators. Embodiments of the present invention are described herein using a correctional institute or prison as an exemplary facility. However, it is to be understood that embodiments of the present invention may be utilized in other types of facilities, e.g., nursing homes, assisted living facilities, schools, camps, etc.

Example embodiments are described herein with reference to graphical user interfaces (GUIs), block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the GUIs, block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the GUIs, block diagrams and/or flowchart block or blocks.

A tangible, non-transitory computer-readable medium may include an electronic, magnetic, optical, electromagnetic, or semiconductor data storage system, apparatus, or device. More specific examples of the computer-readable medium would include the following: a portable computer diskette, a random access memory (RAM) circuit, a read-only memory (ROM) circuit, an erasable programmable read-only memory (EPROM or Flash memory) circuit, a portable compact disc read-only memory (CD-ROM), and a portable digital video disc read-only memory (DVD/Blu-eRay).

The computer program instructions may also be loaded onto a computer and/or other programmable data processing apparatus to cause a series of operational steps to be performed on the computer and/or other programmable apparatus to produce a computer-implemented process such that the instructions which execute on the computer or other programmable apparatus provide steps for implementing the functions/acts specified in the GUIs, block diagrams and/or flowchart block or blocks. Accordingly, embodiments of the present invention may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated. Moreover, although some of the diagrams include arrows on communication paths to show a primary direction of communication, it is to be understood that communication may occur in the opposite direction to the depicted arrows.

Referring now to the figures, systems, methods, and computer program products for predicting which prison inmates in a facility may be vulnerable to rape, and which prison inmates in the facility may be sexual predators, are provided. By predicting the vulnerability/dangerousness of inmates when they are admitted to a facility, inmates can be housed accordingly in the facility. For example, the most dangerous inmates can be kept isolated from others, particularly the most vulnerable, etc.

FIG. 1 is a flowchart of operations for predicting prison inmates who may be vulnerable to rape, and prison inmates who may be sexual predators, according to some embodiments of the present invention. Objective/measurable information is obtained from one or more third party databases (120, FIG. 2) for an inmate as well as from observations of the inmate made by an observer, typically upon arrival at a correctional facility (Block 10). This objective information may include, for example, height, weight, race, sexual orientation, number of criminal charges, nature of criminal charges, etc. Clinical or health information about the inmate is obtained (Block 20) from one or more sources (122, FIG. 2). Inmate health information includes, for example, medical information, mental disease information, medication information, etc. Exemplary sources of inmate health information include databases maintained by hospitals and other healthcare providers, correctional facilities, government agencies, etc.

Subjective information about the inmate is obtained (Block 30) from the inmate and from observations of the inmate by an observer (124, FIG. 2), typically upon arrival at a correctional facility, using a predetermined format. Subjective information includes, for example, the appearance of an inmate to an observer, e.g., physical attractiveness, muscularity, grooming, evidence of anxiety, etc. The various information obtained (i.e., objective, clinical, subjective) may be obtained in any order and/or may be obtained substantially simultaneously. Embodiments of the present invention are not limited to a particular order of information collection.

Figure 2:
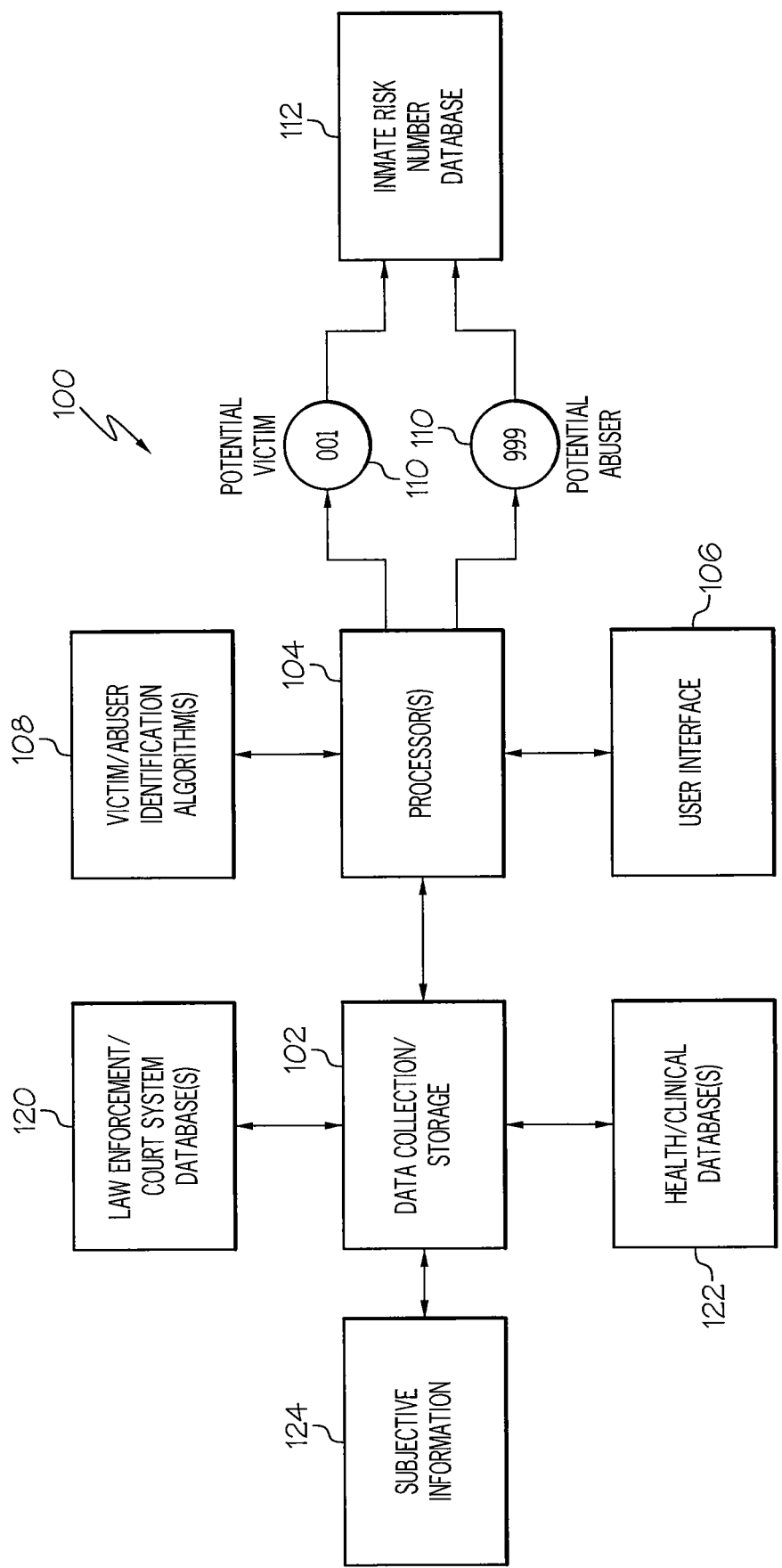
FIG. 2 is a block diagram that illustrates an exemplary system for predicting prison inmates who may be vulnerable to rape, and prison inmates who may be sexual predators, in accordance with embodiments of the present invention.

The objective, health, and subjective information is then processed using one or more victim/abuser identification algorithms (108, FIG. 2) to derive a risk number (110, FIG. 2) for the inmate (Block 40, FIG. 1). For example, on a scale of 0 to 1,000, 0 can represent the most vulnerable inmate and 1,000 can represent the most dangerous sexual predator. However, other scales may be utilized without limitation. Exemplary risk numbers 110 are illustrated in FIG. 2, one that indicates a potential victim (value 001) and one that indicates a potential abuser/predator (value 999). The processing involves assigning weighted values to the acquired objective, clinical, and subjective information. The assigned weights depend on a ranked importance in determining dangerousness or vulnerability. For example, determining an inmate as being perceived as gay or non-traditionally heterosexual would carry tremendous importance in the inmate migrating towards the "potential victim" end of the grading scale as compared to most of the other variables. "Weights" are derived from in depth data study and the application of significant statistical equations.

Other inmates in a facility are then identified who may be a potential victim of this inmate or who may be a potential abuser of this inmate (Block 50, FIG. 1). For example, other inmates having a risk number 110 that falls below a particular vulnerability threshold may be considered potential victims of this inmate. Similarly, other inmates having a risk number 110 that exceeds a particular dangerous threshold may be considered potential abusers/predators of this inmate. The risk number 110 assists a facility (e.g., facility classification staff, facility classification system, etc.) in placing every inmate into a space or setting based on his/her risk—hence predicatively reducing the risk of sexual assault.

FIG. 2 is a block diagram that illustrates an exemplary system 100 for predicting prison inmates who may be vulnerable to rape, and prison inmates who may be sexual predators, in accordance with embodiments of the present invention. The illustrated system 100 includes data collection/storage 102, one or more processors 104, a user interface 106, and one or more victim/abuser identification algorithms 108 that are executable by the processor(s) 104 to generate a risk number 110 for each inmate in a facility. The risk number determined for each inmate is stored, for example, in an inmate risk number database 112. Information collected and stored in data storage 102, and subsequently used by the victim/abuser identification algorithm(s) 108, includes objective information obtained from third party database(s) 120 (e.g., law enforcement databases, court system databases, etc.), clinical/health information obtained from third party databases 122 (e.g., hospital databases, other healthcare provider databases, correctional facility databases, etc.), and subjective information 124 obtained by an observer. The user interface 106 can facilitate communications and data collection from law enforcement/court system databases 120, as well as health/clinical databases 122. In addition, the user interface can be used to enter subjective information 124 by an observer of an inmate.

The overarching intent of the data collection is to capture/generate specific information as it applies to specific inmates, digest the information and subsequently apply formulas whereby a number and, in some embodiments, a color assignment can be applied for a facility caregiver to consider in management decisions of the particular inmate. Once processed, this information can be displayed to specifically authorized individuals within a facility in order to keep the most vulnerable inmates away from the most dangerous inmates. Because prison rape is an act of opportunity, this process does not predict who or when an individual may rape another individual, but may assist a facility in reducing the possibility of rape and similar acts.

A unique aspect of embodiments of the present invention is the ability to capture and blend information from different sources, none of which alone or independently contribute significantly to the predictive nature of determining vulnerable inmates and dangerous inmates. The three categories of data complement one another, but prior to the present invention, information such as that professed by an inmate and observed of an inmate have not been placed into any type of evaluation process in an objective manner.

Objective data in accordance with embodiments of the present invention are data having "fixed characteristics" and may be measured as well as captured, stored, and processed from virtually any database or source (120, FIG. 2). Exemplary objective data include fixed characteristic data about an inmate, such as height, weight, gender, race, sexual orientation, number of criminal charges, nature of criminal charges, etc. Objective data about an inmate can be obtained from state and federal court system databases, state and federal law enforcement databases, as well as from various other databases/sources. Some exemplary databases are listed below in Table 1.

TABLE 1

North Carolina Court System: www.nccourts.org
Criminal Justice Law Enforcement Automated Data Services: cjleads.nc.gov
Law Enforcement Information Exchange: www.linxncr.us
North Carolina Warrant Repository: nccriminallaw.sog.unc.edu Objective data is converted into manageable packets of information that can be used by the victim/abuser identification algorithm(s) (108, FIG. 2). Data relating to predicting risk and dangerousness (e.g., age—evidence in the literature suggests that the younger an inmate is the more likely that that the inmate will be raped or sexually abused) is of particular relevance. Table 2 below summarizes exemplary objective data that may be collected (Block 10, FIG. 1) in accordance with embodiments of the present invention.

TABLE 2

1) Age
2) Race
3) Marital status
4) # of previous incarcerations
5) Violent nature of charges
6) Convictions of sex related crimes against a child or adult
7) Incarcerated strictly for immigration purposes
8) Convictions for physically aggressive sexual act(s)
9) Prior convictions for other violent offenses
10) History of institutional violence and/or sexual offence(s)
11) Gang affiliation Health/clinical data (e.g., inmate behavioral information, inmate medical information, inmate physical information, etc.) is also objective information that may be automatically captured, stored, and processed from virtually any database or source (122, FIG. 2). Exemplary health data also may include dangerousness characteristics, such as whether the person is suicidal, homicidal, has mental or emotional issues, has health issues, takes medications, etc. The health data is converted into manageable packets of information that can be used by the victim/abuser identification algorithm(s) (108, FIG. 2). For example, if someone is identified as having emotional difficulties with tangible evidence of suicidality or homicidality, this information is automatically integrated into the risk number algorithm(s). Table 3 below summarizes exemplary health data that may be collected (Block 20, FIG. 1) in accordance with embodiments of the present invention.

TABLE 3

1) Mental, physical or developmental disability
2) Physical disability
3) Personality disorder-narcissistic, antisocial, dependant, histrionic, borderline,
4) Schizoid spectrum
5) Autistic spectrum
6) Number of psychiatric hospitalizations Subjective or perspective data (124, FIG. 2) generally comes from two sources—the inmate and an observer of the inmate. For example, the inmate will be subjected to questions, which will give the observer indications as to what the inmate's self perceived sexual preference is, how vulnerable the inmate feels in a jail or prison setting, what the inmate's reaction might be under certain circumstances, etc. The inmate will be observed, also, and the observations gathered by a trained corrections officer or medical staff member will be entered into data storage (102, FIG. 2) for use by the victim/abuser identification algorithm(s) (108, FIG. 2). Observed information may include attractiveness, persona, hygiene, interactive style, aggressiveness of personality, anxious personality, etc. Table 4 below summarizes some exemplary observable subjective data that may be collected (Block 30, FIG. 1) and stored for subsequent use in accordance with embodiments of the present invention.

TABLE 4

Figure 3A:
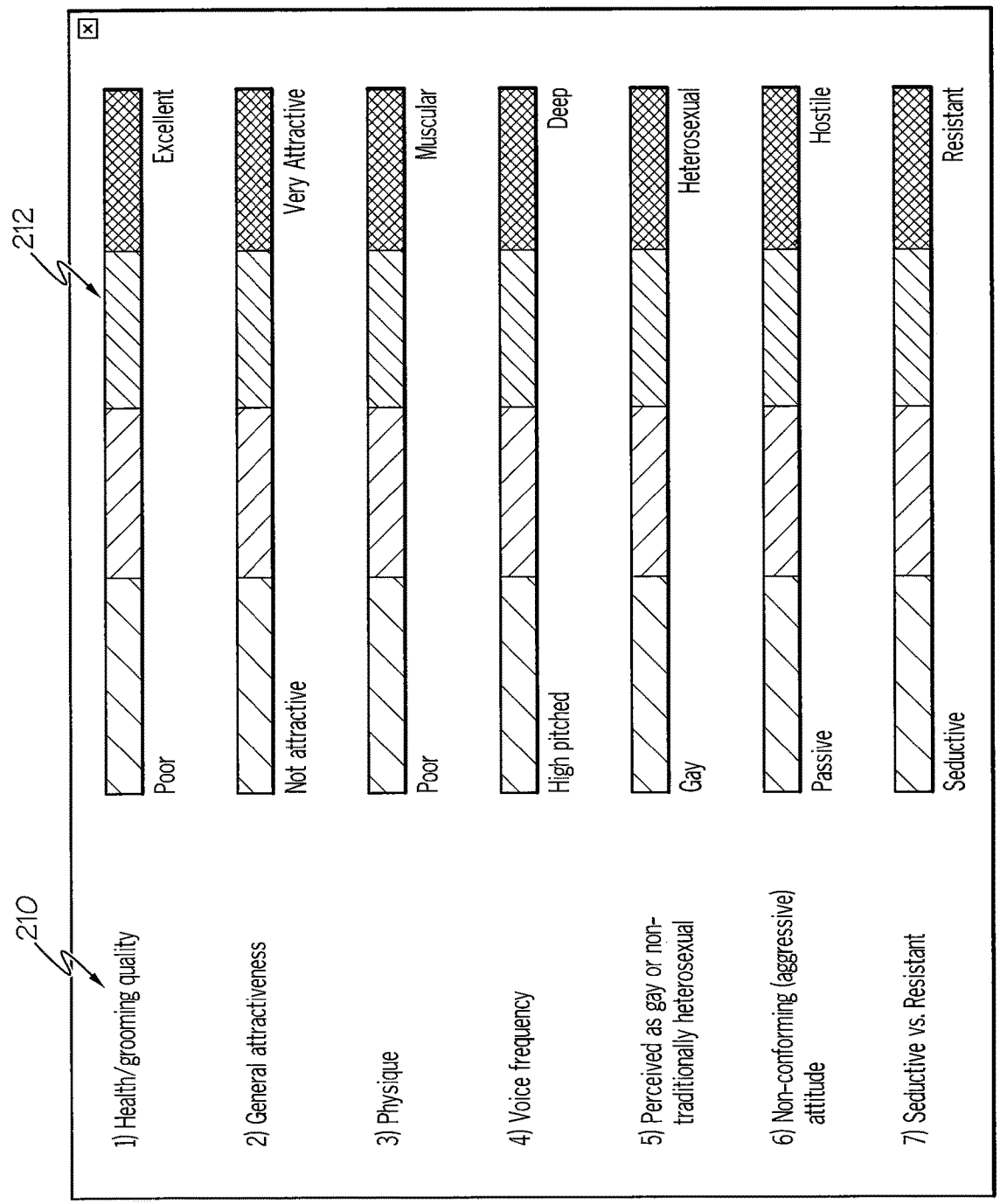
FIG. 3A is a graphical user interface (GUI) illustrating gradient scoring for various observable perspective data, in accordance with embodiments of the present invention.
Figure 3B:
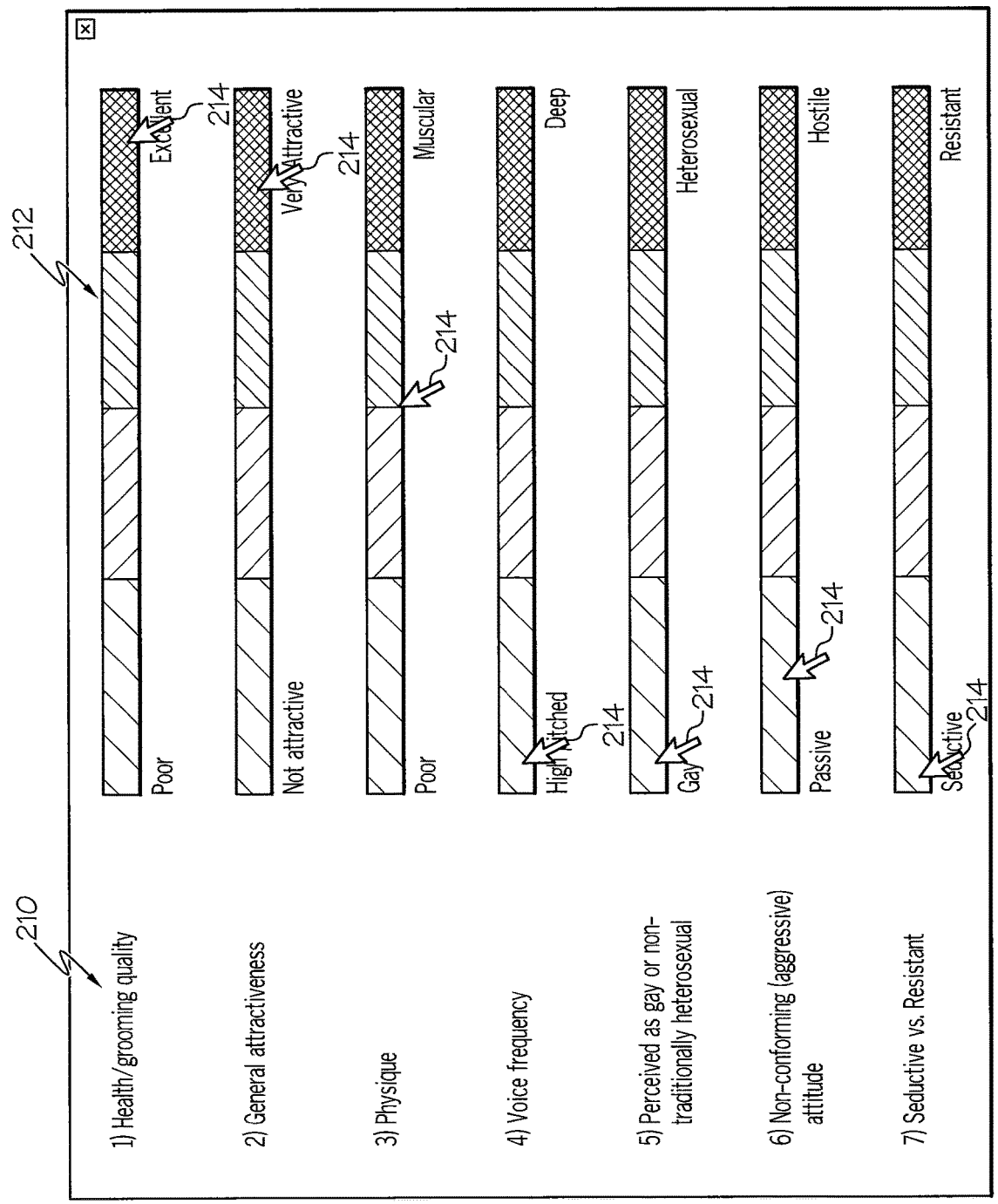
FIG. 3B illustrates the GUI of FIG. 3A after an observer has indicated scores for the various observable perspective data of FIG. 3A for a particular inmate.

1) Health/grooming quality (to include skin quality, hygiene, tattoos/piercings
2) General attractiveness TABLE 4-continued 3) Physique
4) Voice frequency
5) Perceived as gay or non-traditionally heterosexual
6) Non-conforming (aggressive) attitude
7) Seductive vs. resistant FIG. 3A illustrates a list 210 of exemplary observable subjective data along with a scoring scale or gradient 212 for each item. The illustrated list 210 and scoring gradient 212 may be printed on a form or may be in the form of a graphical user interface (GUI) displayed within an electronic device, such as a computer, smartphone, etc. FIG. 3B illustrates the list 210 of FIG. 3A and scoring gradient 212 after an observer has indicated scores (represented by arrows 214 for the various data.

FIG. 4 illustrates a list of topics 220 that are helpful in determining a risk number for an inmate, according to some embodiments of the present invention. Adjacent to each topic in the list 220 are one or more questions 222 that an observer of an inmate can ask the inmate. The illustrated list 220 and respective questions 222 may be printed on a form or may be displayed via a user interface (106, FIG. 2), such as a GUI displayed within an electronic device, such as a computer, smartphone, etc.

Figure 6:
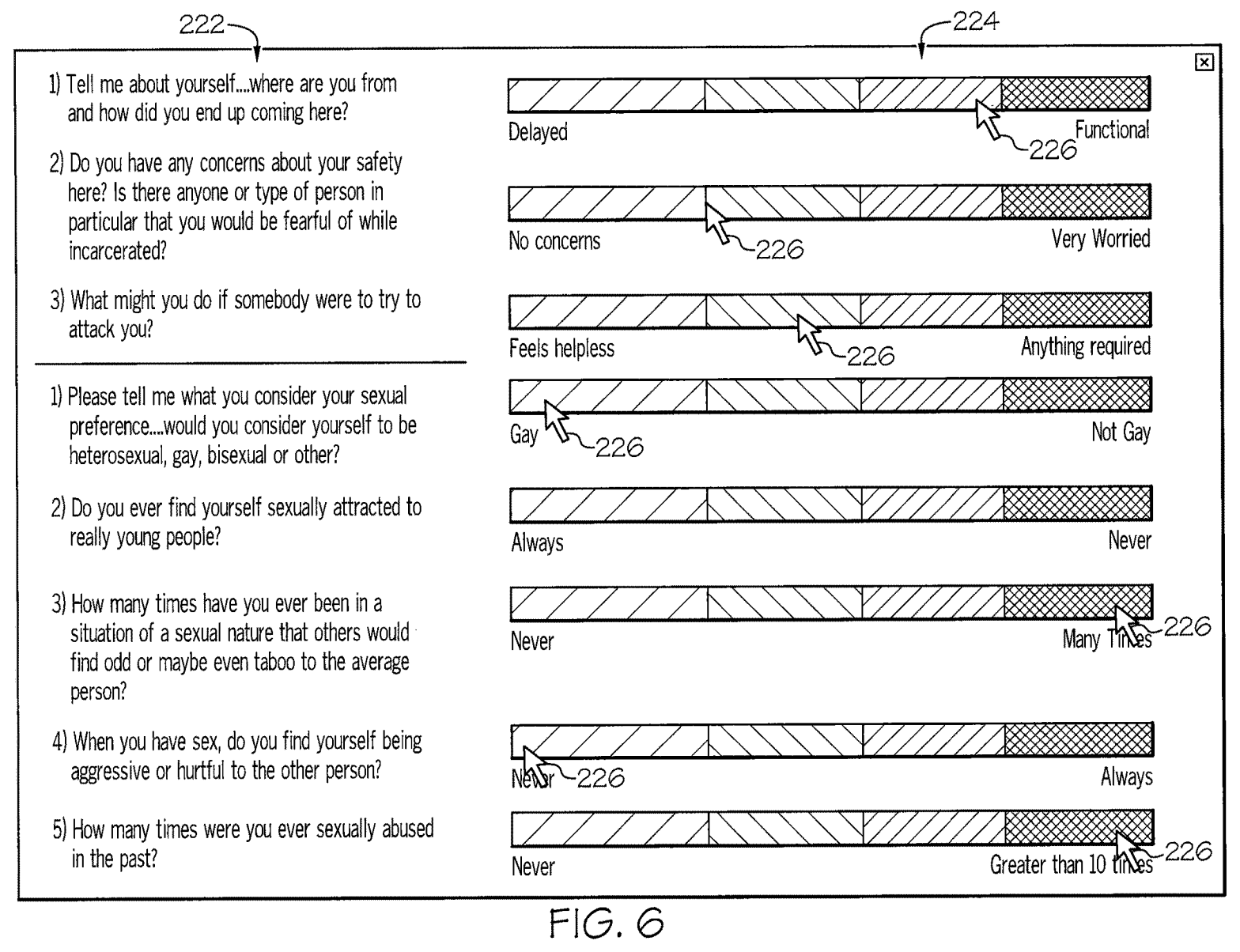

FIG. 5 illustrates the list 222 of questions from FIG. 4 along with a scoring scale or gradient 224 for each question or group of related questions. FIG. 6 illustrates the list 222 of questions and respective scoring gradients 224 after an observer has indicated scores (represented by arrows 226) for the various topics. The various subjective information scores are entered into data storage/collection (102, FIG. 2), for example, manually by an observer, or via a computer, smartphone, etc.

Figure 7A:
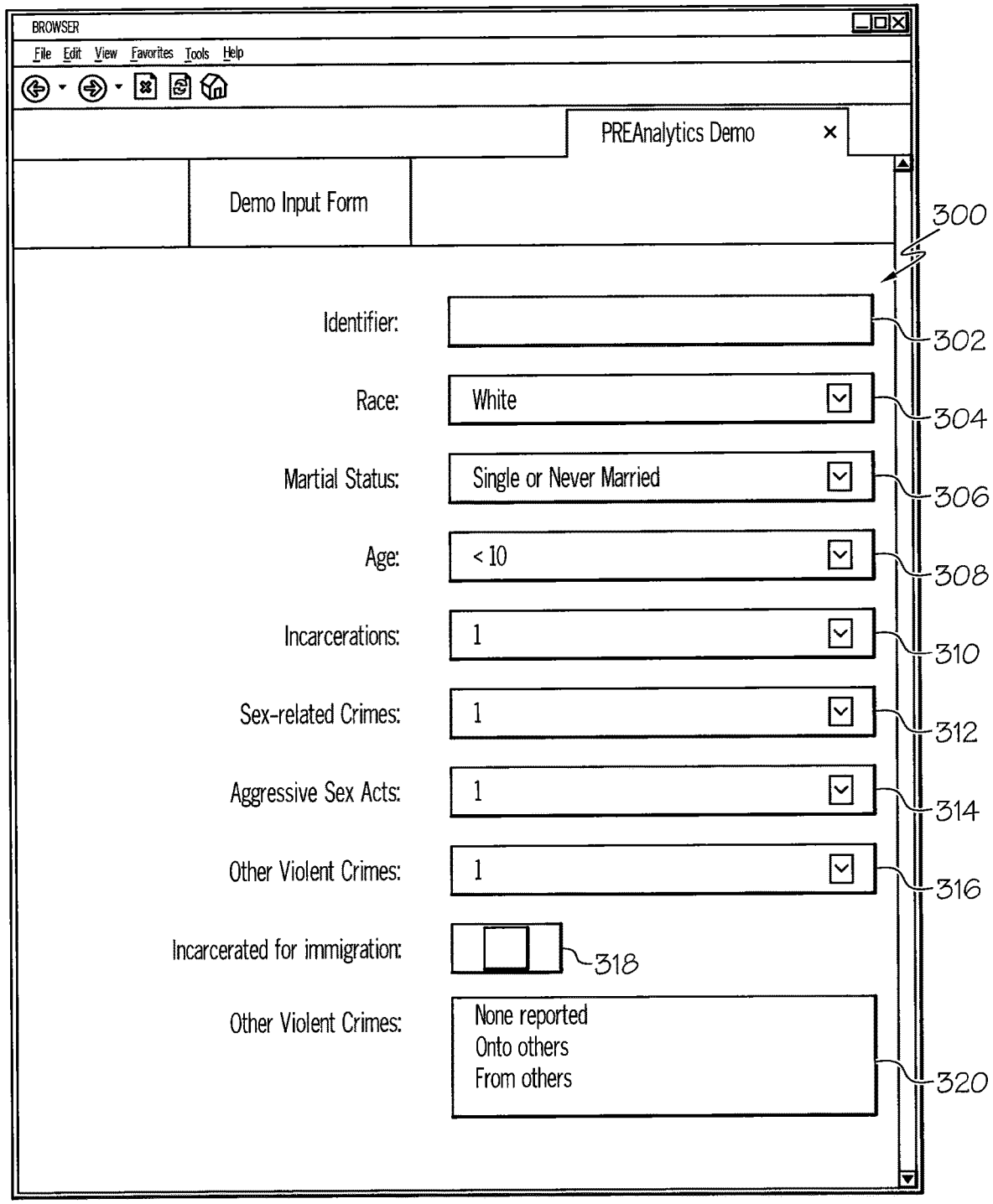
FIGS. 7A-7C are exemplary GUIs for collecting data useful in determining a risk number for an inmate in accordance with some embodiments of the present invention.
Figure 7B:
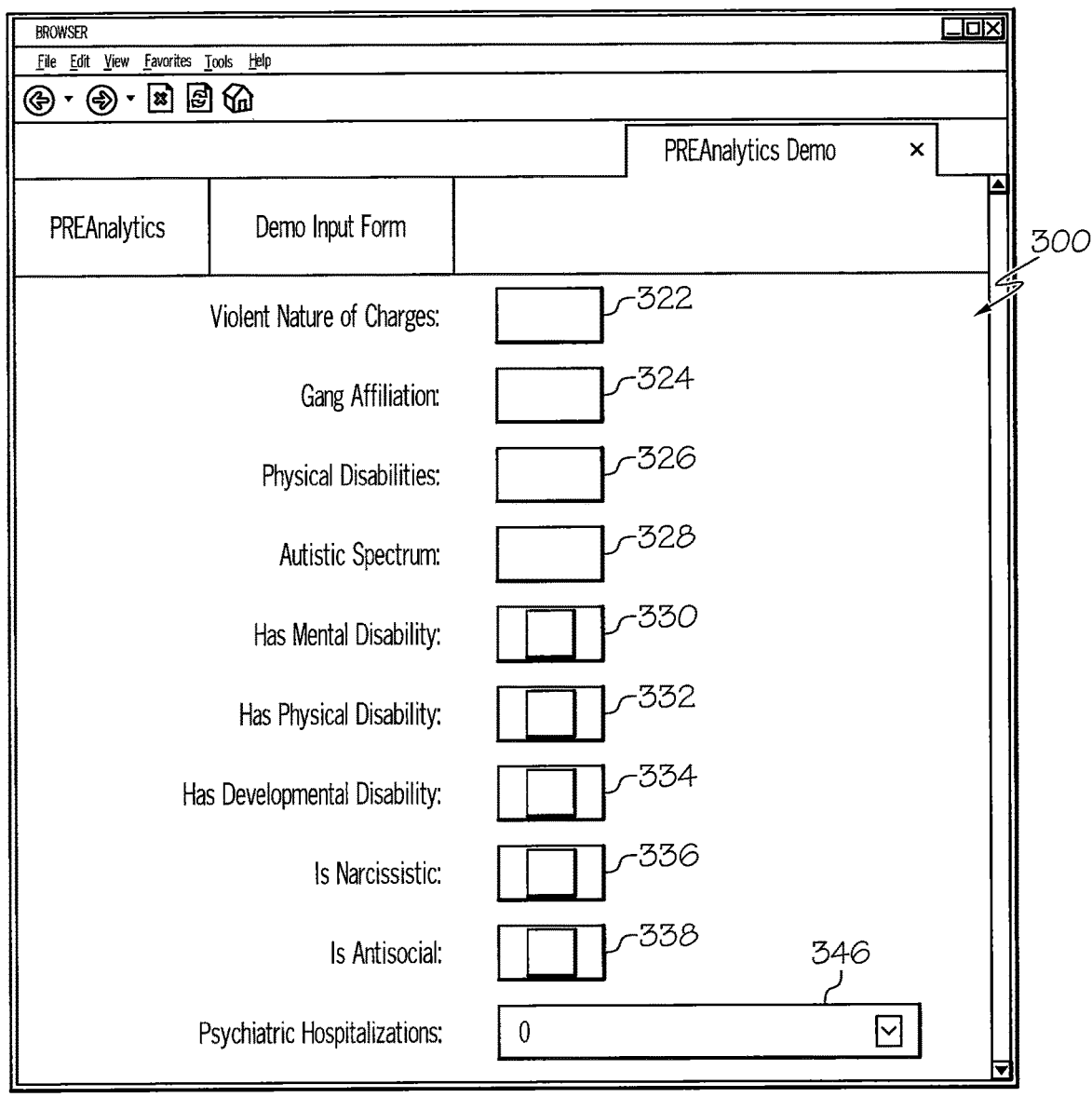
Figure 7C:
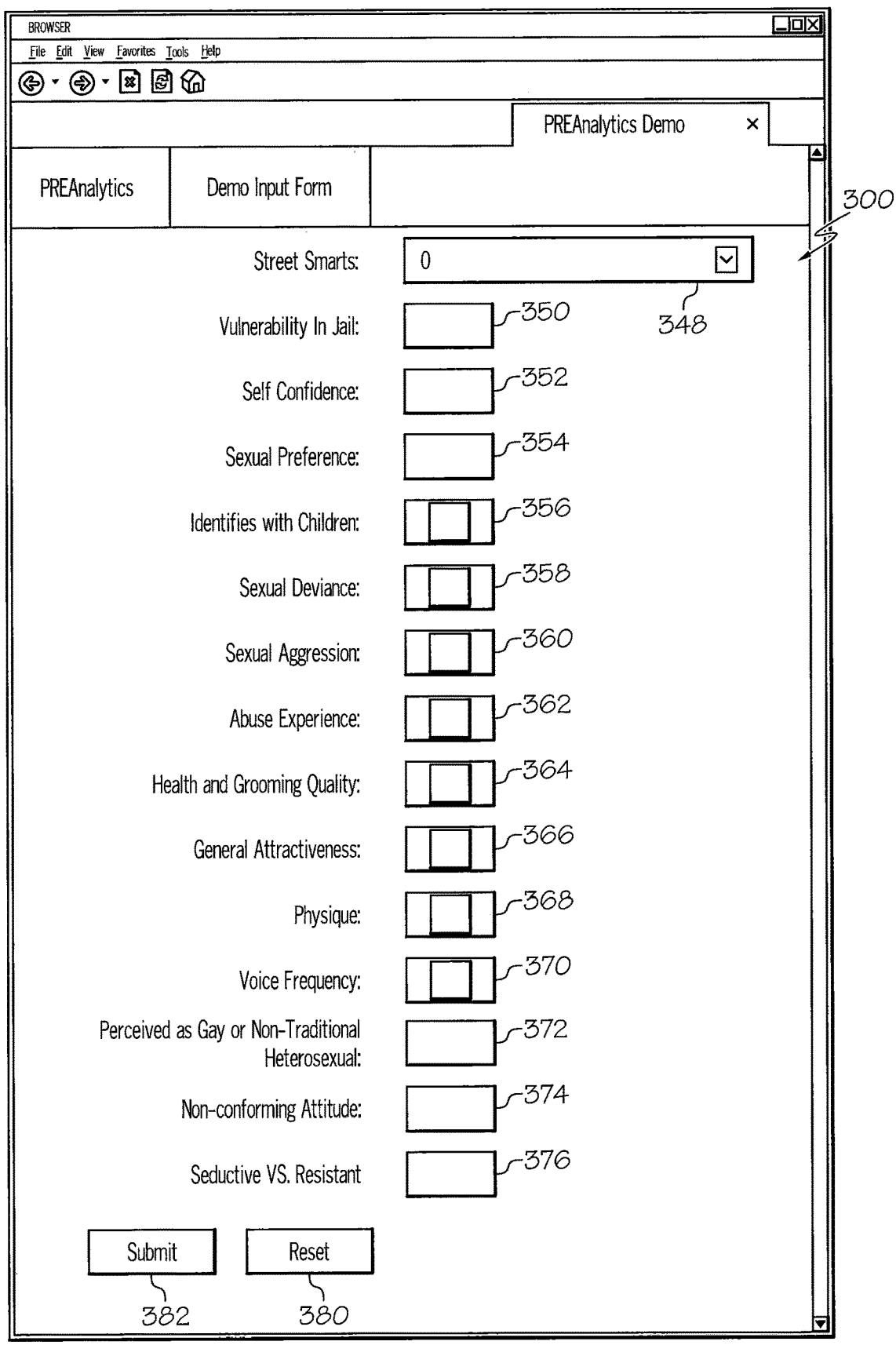

FIGS. 7A-7C illustrate an exemplary GUI 300 that may be utilized in collecting objective and/or subjective information about an inmate in accordance with some embodiments of the present invention. For example, in FIG. 7A, the GUI 300 includes a plurality of user input boxes 302-320 that allow the following information to be entered: inmate identifier 302, inmate race 304, inmate marital status 306, inmate age 308, number of previous incarcerations for the inmate 310, number of sex-related crimes of which the inmate has been accused and/or convicted 312, number of aggressive sex acts of which the inmate has been accused 314, and the number of violent crimes of which the inmate has been accused and/or convicted 316. The GUI 300 illustrated in FIG. 7A also includes a user input box 320 in which the history of an inmate's violence can be input.

The exemplary GUI 300 continues on FIG. 7B with a plurality of user input boxes that allow the following information to be entered: violent nature of charges against the inmate 322, whether the inmate is affiliated with a gang 324, a listing of inmate physical disabilities 326, where the inmate is located on an autism spectrum 328, whether the inmate has a mental disability 330, whether the inmate has a developmental disability 334, whether the inmate is narcissistic 336, whether the inmate is antisocial 338, and the number of psychiatric hospitalizations for the inmate 346.

The exemplary GUI 300 continues on FIG. 7C with a plurality of user input boxes that allow the following information to be entered: street smarts rating 348 (i.e., is totally naïve to current circumstances and all implications thereof (rating=1), understands and appreciates detainment (rating=3), recognizes current circumstances and the implications so as to be dangerous to the facility or others (rating=5), etc.), an indication as to whether the inmate is vulnerable in jail 350, an indication as to whether the inmate has self confidence 352, an indication as to the inmate's sexual preference 354, an indication as to whether the inmate identifies with children 356, an indication as to whether the inmate has sexual deviance 358, an indication as to whether the inmate has sexual aggression 360, an indication as to whether the inmate has abuse experience 362, an indication of the inmate's health and grooming quality 364, an indication of the inmate's general attractiveness 366, an indication of the inmate's physique 368, an indication of the inmate's voice frequency 370, an indication as to whether the inmate is perceived as gay or non-traditional heterosexual 372, an indication as to whether the inmate has a non-conforming attitude 374, and an indication as to whether the inmate is seductive or resistant 376.

The exemplary GUI 300 also includes a GUI control 380 that allows an observer of an inmate to reset information in one or more of the user input boxes 302-376, and also includes a GUI control 382 that allows the observer to submit the information within the user input boxes 302-376 to data storage (102, FIG. 2) and/or directly to the victim/abuser identification algorithm(s) (108, FIG. 2), as would be understood by one skilled in the art of the present invention.

Once the data is assembled and formulated, each variable is given a certain weight as established by review of evidence in the literature and as assigned by a group of thought leaders within the corrections industry. These weights will continually be reviewed and reevaluated for validity over time as more and more data is generated, and as other data sources are added. For example, new variables may be added, old variables may be deleted, and the weights may be changed, for example, depending on future research findings.

According to some embodiments of the present invention, all inmates are started out at an arbitrary score of 500 and, depending upon the variables and weights assigned thereto, the inmate may drop points toward "0" suggesting that they are vulnerable to rape or exploitation, or may increase points toward "1,000" suggesting that the inmate is more of an aggressor. The higher the number, the higher the risk that the inmate may be a potential rapist or perpetrator.

Algorithm Example

Overview

An algorithm, according to embodiments of the present invention, generally speaking, consumes a set of weighted data points as well as a set of actual user data for those data points. It produces two scores on a configurable scale (currently 0 to 1000). One represents how likely the user is to be a rape victim, the other an abuser (rapist). Higher scores mean "more likely to be X", where X is a victim or an abuser.

Procedure for Defining Weights

To clearly explain how weights for the algorithm should be defined, I'll guide the user through a procedure. The goal is to prevent information loss as concepts are translated from data-driven abuser/victim patterns to the language consumed by the algorithm.

Build List of Data Points

Start by creating a simple list of the data points relevant to scoring a user. It's okay if some data points only relate to abuse likelihood, some only to victim likelihood or some to both.

Decide Importance of Data Points

For each data point (DP) on your list, you will now decide their relative importance. You will actually do this twice for each DP, once for the importance to the victim score and once for the importance to the abuser score. The weights you create here are equivalent to the percentage each DP counts when computing the final scores. Since we're thinking about percentages, it's natural to write these weights as values between 0 and 1. For example, assume you only have two DPs. One strongly indicates an abuser (let's call it DPa), the other strongly indicates a victim (let's call it DPv). If the data shows that DPa should count for 95% of the total abuser score, while DPv is only 5% relevant to the likelihood of being an abuser, you would give an abuser weight of 0.95 to DPa and 0.05 to DPv. Note that you can use any number of significant figures, as for every step (for example, 0.87235). The sum of all abuser weights should be exactly 1, as should the sum of all victim weights. Remember, these are percentages.

Decide Types of Data Points

You will now need to decide how the values that each data point can range over should be expressed. For example, should values be a small fixed set of possible options, like "black", "white" and "Asian" for race, where each value should be weighed differently by the algorithm? Or should the values be thought of as ranges, like the age range 31-65? If the values should be thought of as ranges, should the algorithm weigh all values in each range the same? Or should each range have a weight, but higher values in a range score more than lower values in that same range?

Let the data points like the first type, where values are one of a small fixed set of possibilities, be called selection-type DPs. Let the second type, where ranges of values have the same relevance to abuser/victim scores, be called coarse-type DPs. Let the third type, where values are broken into ranges with certain abuser/victim likelihoods and higher values in a range score higher than lower values in the same range, be called fine-type DPs. Label each data point as one of the three types described here.

Enumerate Possible Data Point Values

For each data point, you will now need to describe the values it should range over. For selection-type DPs, you will choose the set of possible choices. For example, consider marital status. A person being scored may be "Married", "Single or Never Married", "Widowed and not Remarried", "Divorced and not Remarried", "Married but Separated", etc.

For coarse-type and fine-type DPs, you will divide the total range of possible values into groups that correlate with abuser/victim likelihoods. For example, the total range of ages is 0 to infinity. That total range may break down into groups like 31-65. Each group should share the same abuser/victim likelihood (remembering the fine-type vs coarse-type distinction described above). As an aside on nomenclature, note that the algorithm calls all of these delineations of values "groups". So, "Married" is a group, <21 is a group, etc.

Also note that the abuser/victim calculations can accept different sets of fine-type and coarse-type DP groups for a given data point. So, if the age groups that work for describing a victim aren't the same as the age groups that describe an abuser, define two sets of groups for that data point. If a group break-down applies to both abusers and victims, only define one set of groups and make a note that it applies to both scores.

Describe the Importance of Each Value Group

For every group described above, you will now need to decide how group membership should affect abuser/victim scores. Think of this as a portion of the weights you assigned each DP in the Decide Importance of Data Points section. You will allocate some percentage of that weight based on group membership.

You will assign each group a value between 0 and 1 (inclusive). Recall that this is simply a convenient way of writing percentages. For example, if there's an abuser age group 21 to 30 that is the most likely to commit rape among all abuser age groups, they should be assigned a 1. If the group 31 to 65 is less likely to commit rape, they might be assigned a 0.6. If the abuser age group >65 is least likely to commit rape, they should be assigned a 0.

Note that this step has implications for the maximum and minimum possible total abuser/victim scores. If for some data point there's no group that's assigned a 1, there's no way for anyone to get the full weight from the Decide Importance of Data Points section, so there's no way anyone can get a maximum score. The same applies to no-group-with-a-0 and the minimum score. This highlights the importance of understanding what the minimum and maximum scores actually mean. Scoring a 0 on the abuser scale doesn't mean that someone has a 0% chance to commit rape, just that they fall into the least likely group to commit rape for every data point.

Combining Expert Input

There are some important points to consider with regard to taking the input of a group of experts, in the form of the output of the process described above, and combining them into a cohesive data set that's ready for consumption by the algorithm.

There are two possible strategies: either the experts come to a consensus on parts of the process, or each expert produces their own output from the above process and we run the algorithm against each, averaging the overall abuser/victim scores produced by each.

The parts of the process that all experts would have to agree on for the first option to work are the choice of data points (Build List of Data Points section), the types of data points (Decide Types of Data Points section) and the groups DP values fall into (Enumerate Possible Data Point Values section). If those parts of the process are standard across experts, the weights produced in the Decide Importance of Data Points and the Describe the Importance of Each Value Group sections can simply be averaged.

If each expert produced their own independent output that differs in any of the three sections described above, the algorithm can be modified to accept >1 configurations, produce abuser/victim scores for each and average the results to produce the final scores.

Table 5 below illustrates exemplary data points and weights for use in determining a risk number for a person, wherein the risk number represents a risk of the person being a sexual predator, according to some embodiments of the present invention.

TABLE 5

Example Algorithm Weight Final Score - Abuser

| DP Weight | DP Type | Groups: Group Weights | | Data Point |
|---|---|---|---|---|
| 0.038 | S | | | Race: |
| | | | 0.35 | Mixed race |
| | | | 0.35 | White |
| | | | 1.00 | Black or African-American |
| | | | 1.00 | Hispanic |
| | | | 0.20 | Native Hawaiian or other |
| | | | 0.20 | Pacific Islander |
| | | | 0.20 | American Indian or Alaska native |
| | | | 0.00 | Asian |
| 0.027 | S | | | Marital Status: |
| | | | 1.00 | Single or never married |
| | | | 0.00 | Married |
| | | | 0.80 | Widowed and not remarried |
| | | | 0.80 | Divorced and not remarried |
| | | | 0.20 | Married but separated |
| 0.048 | C | | | Age: 0-infinity |
| | | 0-17 | 0.00 | |
| | | 18-35 | 1.00 | |
| | | 36-45 | 0.50 | |
| | | 46 or > | 0.20 | |
| 0.054 | F | | | Incarcerations: 1->4 |
| | | 1 | 0.00 | |
| | | 2 | 0.50 | |
| | | 3 | 0.80 | |
| | | 4 | 0.90 | |
| | | >4 | 1.00 | |
| 0.037 | C | | | Years Sentenced: |
| | | | 0.00 | <1 |
| | | | 0.50 | 1-4 years |
| | | | 0.80 | 5-14 years |
| | | | 1.00 | >15 (eligible for parole) |
| | | | 1.00 | Sentenced to Life |
| 0.010 | S | | | Pretrial: |
| | | | 0.00 | Yes |
| | | | 1.00 | No |

TABLE 5-continued

Example Algorithm Weight Final Score - Abuser

| DP Weight | DP Type | Groups: Group Weights | | Data Point |
|---|---|---|---|---|
| 0.050 | F | | | Sex-Related Crimes: |
| | | 0 | 0.00 | 0 |
| | | 1 | 0.30 | >3 |
| | | 2 | 0.90 | |
| | | 3 | 1.00 | |
| | | >3 | 1.00 | |
| 0.050 | F | | | Aggressive Sex Acts: |
| | | 0 | 0.00 | 0 |
| | | 1 | 0.70 | >3 |
| | | 2 | 0.80 | |
| | | 3 | 0.90 | |
| | | >3 | 1.00 | |
| 0.038 | F | | | Other Violent Crimes: |
| | | 0 | 0.00 | 0 |
| | | 1 | 0.60 | >3 |
| | | 2 | 0.80 | |
| | | 3 | 0.90 | |
| | | >3 | 1.00 | |
| 0.003 | S | | | Incarcerated for Immigration: |
| | | | 0.00 | Yes |
| | | | 1.00 | No |
| 0.077 | S | | | History of Violence: |
| | | | 0.00 | No history of violence reported |
| | | | 1.00 | History of violence onto others |
| | | | 0.80 | History of violence from others |
| | | | 0.90 | History of violence from and to others |
| 0.034 | F | | | Violent Nature of Charges: |
| | | 1 | 0.00 | 1 - None (theft, embezzlement, trespassing, etc.) |
| | | 2 | 0.25 | 3 - Moderate (breaking and entering, strong-arm robbery, resistance to arrest, assault, etc.) |
| | | 3 | 0.50 | |
| | | 4 | 0.90 | |
| | | 5 | 1.00 | |
| | | | | 5 - Severe (murder, attempted murder, armed robbery, rape, etc.) |
| 0.025 | F | | | Gang Affiliation: |
| | | 1 | 0.00 | 1 - None obvious |
| | | 2 | 0.25 | 3 - Some evidence of gang affiliation |
| | | 3 | 0.50 | 5 - Obvious gang affiliation and participation |
| | | 4 | 0.90 | |
| | | 5 | 1.00 | |
| 0.025 | F | | | Physical Disabilities: |
| | | 1 | 0.00 | 1 - None obvious |
| | | 2 | 0.40 | 3 - Some impairment evident (examples: limping and/or with some weakness, etc.) |
| | | 3 | 0.20 | |
| | | 4 | 0.00 | |
| | | 5 | 0.00 | 5 - Obvious impairment evident (examples: needs assistance to walk, uses cane, uses wheelchair, physically frail, etc.) |
| 0.007 | F | | | Interactions with Others: |
| | | 1 | 1.00 | 1 - Overly engaging, patronizing, intrusive |
| | | 2 | 0.90 | 3 - Normal interactions, able to conversate |
| | | 3 | 0.80 | |
| | | 4 | 0.00 | |
| | | 5 | 0.00 | 5 - Obvious inability to normally engage in conversation with others or emotionally distant/loss of 'human' qualities |
| 0.030 | F | | | Has Developmental Disability: |
| | | 1 | 1.00 | 1 - None evident |
| | | 2 | 0.80 | 3 - Appears somewhat delayed/mentally slow |
| | | 3 | 0.40 | |
| | | 4 | 0.00 | 5 - Obviously severely delayed/mentally challenged |
| | | 5 | 0.00 | |
| 0.057 | F | | | Self Importance: |
| | | 1 | 0.00 | 1 - Appropriate with needs/concerned for others evident |
| | | 2 | 0.20 | 3 - Projects needs/appears to have expectations beyond the normal |
| | | 3 | 0.60 | |
| | | 4 | 0.09 | |
| | | 5 | 1.00 | 5 - Extremely selfish, obviously takes advantage of others without remorse |

TABLE 5-continued

Example Algorithm Weight Final Score - Abuser

| DP Weight | DP Type | Groups: | Group Weights | Data Point |
|---|---|---|---|---|
| 0.039 | F | | | Psychiatric Hospitalizations: 0->3 |
| | | 0 | 1.00 | |
| | | 1 | 0.90 | |
| | | 2 | 0.70 | |
| | | 3 | 0.50 | |
| | | >3 | 0.00 | |
| 0.029 | F | | | Street Smarts: |
| | | 1 | 0.00 | 1 - Totally naive to current |
| | | 2 | 0.00 | circumstances and all implications |
| | | 3 | 0.05 | thereof |
| | | 4 | 0.09 | 3 - Understands and appreciates |
| | | 5 | 1.00 | detainment |
| | | | | 5 - Recognizes current circumstances and the implications so as to be dangerous to the facility or others |
| 0.031 | C | | | Age of First Sexual Experience: |
| | | | 1.00 | 5-12 |
| | | | 0.09 | 13-15 |
| | | | 0.07 | 16-36 |
| | | | 0.00 | >36 |
| | | | 0.00 | Or professes to have never had sexual activity |
| 0.041 | F | | | Vulnerability in Jail: |
| | | 1 | 1.00 | 1 - None appreciated |
| | | 2 | 0.90 | 3 - Appropriately concerned |
| | | 3 | 0.50 | 5 - Extremely fearful, panicking of notion |
| | | 4 | 0.00 | of being incarcerated |
| | | 5 | 0.00 | |
| 0.017 | S | | | Sexual Preference: |
| | | 1 | 0.00 | 1 - Females only |
| | | 2 | 0.90 | 2 - Females preferred |
| | | 3 | 0.90 | 3 - Females and/or males |
| | | 4 | 0.90 | 4 - Males preferred |
| | | 5 | 1.00 | 5 - Males only |
| 0.013 | F | | | Sexually Identifies with Children: |
| | | 1 | 1.00 | 1 - Sexual contact with children |
| | | 2 | 0.00 | unthinkable |
| | | 3 | 0.90 | 3 - Sometimes thinks of younger people |
| | | 4 | 0.90 | as related to sexual circumstances |
| | | 5 | 0.90 | 5 - Always prefers young sexual partners |
| 0.032 | F | | | Sexual Deviance: |
| | | 1 | 0.00 | 1 - No abnormal/bizarre sexual |
| | | 2 | 0.40 | fantasies appreciated |
| | | 3 | 0.80 | 3 - Sometimes thinks of |
| | | 4 | 0.90 | abnormal/bizarre sexual fantasies |
| | | 5 | 1.00 | 5 - Always uses abnormal/bizarre sexual fantasies during sexual thoughts/experiences |
| 0.042 | F | | | Sexual Aggression: |
| | | 1 | 0.00 | 1 - No abnormal/bizarre sexual |
| | | 2 | 0.20 | aggression appreciated |
| | | 3 | 0.60 | 3 - Sometimes thinks of aggression |
| | | 4 | 0.90 | during sex or fantasy |
| | | 5 | 1.00 | 5 - Always prefers aggression during sexual thoughts/experiences |
| 0.021 | F | | | Abuse Experience: |
| | | 1 | 0.00 | 1 - None |
| | | 2 | 0.05 | 3 - Exposed to abuse at times in past |
| | | 3 | 0.07 | 5 - Professes to have been repeatedly |
| | | 4 | 0.09 | and severely abused in all matters to |
| | | 5 | 1.00 | include sexually |
| 0.016 | F | | | Health and Grooming Quality: |
| | | 1 | 1.00 | 1 - Extremely disheveled, filthy and |
| | | 2 | 0.90 | physically ill in appearance |
| | | 3 | 0.80 | 3 - Average health and grooming |
| | | 4 | 0.70 | 5 - Supremely groomed with good |
| | | 5 | 0.00 | hygiene and appearance of vibrant health |
| 0.016 | F | | | General Attractiveness: |
| | | 1 | 1.00 | 1 - Physically disfigured or repulsive in |
| | | 2 | 0.90 | appearance |
| | | 3 | 0.80 | 3 - Average in appearance |
| | | 4 | 0.70 | 5 - Carries characteristics that generate |
| | | 5 | 0.00 | an obvious attractiveness from others |

TABLE 5-continued

Example Algorithm Weight Final Score - Abuser

| DP Weight | DP Type | Groups: | Group Weights | Data Point |
|---|---|---|---|---|
| 0.015 | F | | | Voice Frequency: |
| | | 1 | 0.00 | 1 - With weak, high-pitched and almost |
| | | 2 | 0.20 | imperceptible voice responses |
| | | 3 | 0.70 | 3 - Average speaking tones |
| | | 4 | 0.90 | 5 - With booming and deep, vibrant |
| | | 5 | 1.00 | voice qualities |
| 0.022 | F | | | Physique: |
| | | 1 | 0.00 | 1 - Extremely physically weak in |
| | | 2 | 0.20 | appearance |
| | | 3 | 0.70 | 3 - Average in appearance |
| | | 4 | 0.90 | 5 - Extremely well nourished with |
| | | 5 | 1.00 | bounding musculature |
| 0.014 | F | | | Perceived as Gay or Non-Traditional Heterosexual: |
| | | 1 | 0.00 | 1 - Effeminate or with characteristics |
| | | 2 | 0.20 | opposite of "manly" |
| | | 3 | 0.70 | 3 - Average sexual qualities |
| | | 4 | 0.90 | 5 - With strong "manly" qualities |
| | | 5 | 1.00 | |
| 0.017 | F | | | Non-Conforming Attitude: |
| | | 1 | 0.00 | 1 - Absolutely no resistance to requests |
| | | 2 | 0.30 | or demands |
| | | 3 | 0.70 | 3 - Some resistance noted either openly |
| | | 4 | 0.90 | or passively |
| | | 5 | 1.00 | 5 - Resist request or commands on all occasions either openly or passively |
| 0.015 | F | | | Seductive vs. Resistant: |
| | | 1 | 1.00 | 1 - Makes attempts to engage others for |
| | | 2 | 0.80 | self gratification |
| | | 3 | 0.60 | 3 - Average interactions noted |
| | | 4 | 0.30 | 5 - Proactively distances self from all |
| | | 5 | 0.00 | advances by others who may cause harm |

Table 6 below illustrates exemplary data points and weights for use in determining a risk number for a person, wherein the risk number represents a risk of the person being vulnerable to sexual abuse, according to some embodiments of the present invention.

TABLE 6

Example Algorithm Weight Final Score - Victim

| DP Weight | DP Type | Groups: Group Weights | | Data Point |
|---|---|---|---|---|
| 0.027 | S | | | Race: |
| | | | 1.00 | Mixed race |
| | | | 1.00 | White |
| | | | 0.00 | Black or African-American |
| | | | 0.00 | Hispanic |
| | | | 0.30 | Native Hawaiian or other |
| | | | 0.30 | Pacific Islander |
| | | | 0.30 | American Indian or Alaska native |
| | | | 0.30 | Asian |
| 0.013 | S | | | Marital Status: |
| | | | 1.00 | Single or never married |
| | | | 0.00 | Married |
| | | | 0.50 | Widowed and not remarried |
| | | | 0.50 | Divorced and not remarried |
| | | | 0.50 | Married but separated |
| 0.042 | C | | | Age: 0-infinity |
| | | 0-17 | 0.00 | |
| | | 17-35 | 1.00 | |
| | | 36 or > | 0.50 | |
| 0.028 | F | | | Incarcerations: 1->4 |
| | | 1 | 1.00 | |
| | | 2 | 0.70 | |
| | | 3 | 0.50 | |
| | | 4 | 0.30 | |
| | | >4 | 0.00 | |

TABLE 6-continued

Example Algorithm Weight Final Score - Victim

| DP Weight | DP Type | Groups: Group Weights | | Data Point |
|---|---|---|---|---|
| 0.024 | C | | | Years Sentenced: |
| | | | 1.00 | <1 |
| | | | 0.90 | 1-4 years |
| | | | 0.80 | 5-14 years |
| | | | 0.60 | >15 (eligible for parole) |
| | | | 0.00 | Sentenced to Life |
| 0.014 | S | | | Pretrial: |
| | | | 1.00 | Yes |
| | | | 0.00 | No |
| 0.020 | F | | | Sex-Related Crimes: |
| | | 0 | 0.00 | 0 |
| | | 1 | 0.50 | >3 |
| | | 2 | 0.70 | |
| | | 3 | 0.90 | |
| | | >3 | 1.00 | |
| 0.021 | F | | | Aggressive Sex Acts: |
| | | 0 | 1.00 | 0 |
| | | 1 | 0.90 | >3 |
| | | 2 | 0.50 | |
| | | 3 | 0.20 | |
| | | >3 | 0.00 | |
| 0.013 | F | | | Other Violent Crimes: |
| | | 0 | 1.00 | 0 |
| | | 1 | 0.90 | >3 |
| | | 2 | 0.50 | |
| | | 3 | 0.20 | |
| | | >3 | 0.00 | |
| 0.003 | S | | | Incarcerated for Immigration: |
| | | | 1.00 | Yes |
| | | | 0.00 | No |
| 0.025 | S | | | History of Violence: |
| | | | 0.00 | No history of violence reported |
| | | | 0.50 | History of violence onto others |
| | | | 1.00 | History of violence from others |
| | | | 0.90 | History of violence from and to others |
| 0.011 | F | | | Violent Nature of Charges: |
| | | 1 | 1.00 | 1 - None (theft, embezzlement, trespassing, etc.) |
| | | 2 | 0.90 | |
| | | 3 | 0.70 | 3 - Moderate (breaking and entering, strong-arm robbery, resistance to arrest, assault, etc.) |
| | | 4 | 0.20 | |
| | | 5 | 0.00 | |
| | | | | 5 - Severe (murder, attempted murder, armed robbery, rape, etc.) |
| 0.021 | F | | | Gang Affiliation: |
| | | 1 | 1.00 | 1 - None obvious |
| | | 2 | 0.90 | 3 - Some evidence of gang affiliation |
| | | 3 | 0.70 | 5 - Obvious gang affiliation and participation |
| | | 4 | 0.40 | |
| | | 5 | 0.00 | |
| 0.051 | F | | | Physical Disabilities: |
| | | 1 | 0.00 | 1 - None obvious |
| | | 2 | 0.60 | 3 - Some impairment evident (examples: limping and/or with some weakness, etc.) |
| | | 3 | 0.80 | |
| | | 4 | 0.90 | 5 - Obvious impairment evident (examples: needs assistance to walk, uses cane, uses wheelchair, physically frail, etc.) |
| | | 5 | 1.00 | |
| 0.030 | F | | | Interactions with Others: |
| | | 1 | 1.00 | 1 - Overly engaging, patronizing, intrusive |
| | | 2 | 0.80 | 3 - Normal interactions, able to conversate |
| | | 3 | 0.00 | |
| | | 4 | 0.80 | 5 - Obvious inability to normally engage in conversation with others or emotionally distant/loss of 'human' qualities |
| | | 5 | 1.00 | |
| 0.059 | F | | | Has Developmental Disability: |
| | | 1 | 0.00 | 1 - None evident |
| | | 2 | 0.60 | 3 - Appears somewhat delayed/mentally slow |
| | | 3 | 0.80 | |
| | | 4 | 0.90 | 5 - Obviously severely delayed/mentally challenged |
| | | 5 | 1.00 | |

TABLE 6-continued

Example Algorithm Weight Final Score - Victim

| DP Weight | DP Type | Groups: Group | Weights | Data Point |
|---|---|---|---|---|
| 0.030 | F | | | Self Importance: |
| | | 1 | 1.00 | 1 - Appropriate with needs/concerned for others evident |
| | | 2 | 0.80 | |
| | | 3 | 0.00 | 3 - Projects needs/appears to have expectations beyond the normal |
| | | 4 | 0.80 | |
| | | 5 | 1.00 | 5 - Extremely selfish, obviously takes advantage of others without remorse |
| 0.080 | F | | | Psychiatric Hospitalizations: 0->3 |
| | | 0 | 0.00 | |
| | | 1 | 0.50 | |
| | | 2 | 0.80 | |
| | | 3 | 1.00 | |
| | | >3 | 1.00 | |
| 0.015 | F | | | Street Smarts: |
| | | 1 | 1.00 | 1 - Totally naive to current circumstances and all implications thereof |
| | | 2 | 0.90 | |
| | | 3 | 0.70 | 3 - Understands and appreciates detainment |
| | | 4 | 0.50 | |
| | | 5 | 0.00 | 5 - Recognizes current circumstances and the implications so as to be dangerous to the facility or others |
| 0.017 | C | | | Age of First Sexual Experience: |
| | | | 1.00 | 5-12 |
| | | | 0.90 | 13-15 |
| | | | 0.80 | 16-36 |
| | | | 0.00 | >36 |
| | | | 1.00 | Or professes to have never had sexual activity |
| 0.077 | F | | | Vulnerability in Jail: |
| | | 1 | 0.00 | 1 - None appreciated |
| | | 2 | 0.30 | 3 - Appropriately concerned |
| | | 3 | 0.70 | 5 - Extremely fearful, panicking of notion of being incarcerated |
| | | 4 | 0.90 | |
| | | 5 | 1.00 | |
| 0.025 | S | | | Sexual Preference: |
| | | 1 | 0.00 | 1 - Females only |
| | | 2 | 0.70 | 2 - Females preferred |
| | | 3 | 0.80 | 3 - Females and/or males |
| | | 4 | 0.90 | 4 - Males preferred |
| | | 5 | 1.00 | 5 - Males only |
| 0.019 | F | | | Sexually Identifies with Children: |
| | | 1 | 0.00 | 1 - Sexual contact with children unthinkable |
| | | 2 | 0.70 | |
| | | 3 | 0.80 | 3 - Sometimes thinks of younger people as related to sexual circumstances |
| | | 4 | 0.90 | |
| | | 5 | 1.00 | 5 - Always prefers young sexual partners |
| 0.024 | F | | | Sexual Deviance: |
| | | 1 | 0.00 | 1 - No abnormal/bizarre sexual fantasies appreciated |
| | | 2 | 0.70 | |
| | | 3 | 0.80 | 3 - Sometimes thinks of abnormal/bizarre sexual fantasies |
| | | 4 | 0.90 | |
| | | 5 | 1.00 | 5 - Always uses abnormal/bizarre sexual fantasies during sexual thoughts/experiences |
| 0.029 | F | | | Sexual Aggression: |
| | | 1 | 0.00 | 1 - No abnormal/bizarre sexual aggression appreciated |
| | | 2 | 0.70 | |
| | | 3 | 0.80 | 3 - Sometimes thinks of aggression during sex or fantasy |
| | | 4 | 0.90 | |
| | | 5 | 1.00 | 5 - Always prefers aggression during sexual thoughts/experiences |
| 0.044 | F | | | Abuse Experience: |
| | | 1 | 0.00 | 1 - None |
| | | 2 | 0.60 | 3 - Exposed to abuse at times in past |
| | | 3 | 0.80 | 5 - Professes to have been repeatedly and severely abused in all matters to include sexually |
| | | 4 | 0.90 | |
| | | 5 | 1.00 | |
| 0.030 | F | | | Health and Grooming Quality: |
| | | 1 | 0.00 | 1 - Extremely disheveled, filthy and physically ill in appearance |
| | | 2 | 0.20 | |
| | | 3 | 0.90 | 3 - Average health and grooming |
| | | 4 | 0.90 | 5 - Supremely groomed with good hygiene and appearance of vibrant health |
| | | 5 | 1.00 | |

TABLE 6-continued

Example Algorithm Weight Final Score - Victim

| DP Weight | DP Type | Groups: Group Weights | | Data Point |
|---|---|---|---|---|
| 0.040 | F | | | General Attractiveness: |
| | | 1 | 0.00 | 1 - Physically disfigured or repulsive in |
| | | 2 | 0.30 | appearance |
| | | 3 | 0.90 | 3 - Average in appearance |
| | | 4 | 0.90 | 5 - Carries characteristics that generate |
| | | 5 | 1.00 | an obvious attractiveness from others |
| 0.028 | F | | | Voice Frequency: |
| | | 1 | 1.00 | 1 - With weak, high-pitched and almost |
| | | 2 | 0.90 | imperceptible voice responses |
| | | 3 | 0.80 | 3 - Average speaking tones |
| | | 4 | 0.20 | 5 - With booming and deep, vibrant voice |
| | | 5 | 0.00 | qualities |
| 0.034 | F | | | Physique: |
| | | 1 | 1.00 | 1 - Extremely physically weak in |
| | | 2 | 0.90 | appearance |
| | | 3 | 0.80 | 3 - Average in appearance |
| | | 4 | 0.60 | 5 - Extremely well nourished with |
| | | 5 | 0.00 | bounding musculature |
| 0.064 | F | | | Perceived as Gay or Non-Traditional Heterosexual: |
| | | 1 | 1.00 | 1 - Effeminate or with characteristics |
| | | 2 | 0.90 | opposite of "manly" |
| | | 3 | 0.80 | 3 - Average sexual qualities |
| | | 4 | 0.40 | 5 - With strong "manly" qualities |
| | | 5 | 0.00 | |
| 0.020 | F | | | Non-Conforming Attitude: |
| | | 1 | 1.00 | 1 - Absolutely no resistance to requests |
| | | 2 | 0.90 | or demands |
| | | 3 | 0.60 | 3 - Some resistance noted either openly |
| | | 4 | 0.40 | or passively |
| | | 5 | 0.00 | 5 - Resist request or commands on all occasions either openly or passively |
| 0.026 | F | | | Seductive vs. Resistant: |
| | | 1 | 1.00 | 1 - Makes attempts to engage others for |
| | | 2 | 0.80 | self gratification |
| | | 3 | 0.00 | 3 - Average interactions noted |
| | | 4 | 0.80 | 5 - Proactively distances self from all |
| | | 5 | 1.00 | advances by others who may cause harm |

Risk Number Examples

The two following vignettes exemplifies two inmates (Inmate 1 an Inmate 2) who could be evaluated in accordance with embodiments of the present invention:

Inmate 1

17-year-old Caucasian male not incarcerated for immigration purposes;
Greater than 1 arrest in past for nonviolent crimes including sexual assaults on children
Professes to be naïve to the corrections system and fearful for his safety;
He is very attractive and patronizing in seductive ways;
He has extremely good hygiene and grooming qualities;
He is slightly built and follows commands without questioning authority;
Has known diagnoses of depression, anxiety and drug dependence including cocaine and heroin.

Inmate 2

23-year-old male of mixed-racial dissent not incarcerated for immigration purposes;
Greater than 10 arrests in past for violent crimes including murder against adults and children;
Carries charges of greater than 10 sexual related crimes including rape against both adults and children;
Known to perpetrate sexual assaults on other inmates during all previous incarcerations;
Diagnosed with antisocial personality disorder and a history of drug dependence on cocaine, methamphetamine and opiates;
Has obvious grotesque facial features;
Has large, muscular frame;
Is arrogant and argumentative openly to corrections staff;
Did not respond to punitive measures in correction settings in past;
Manipulative of other inmates;
Known gang affiliation;
History of assault on females in previous relationships.

Because aggressive sexual behaviors in corrections facilities are acts of opportunity, both Inmate 1 and Inmate 2 would potentially be at risk for being either an abuser and/or a victim at any given time. Accordingly, both of their risk numbers would be derived understanding this concept.

Inmate 1 (after addressing all of the DPs) would have a risk number of being an abuser of around 400 and a risk number of being a victim of greater than 800. Accordingly, Inmate 2 (after addressing all of the DPs) would have a risk number of being an abuser of greater than 900 and a risk number of being a victim of 300 or less.

As every correctional facility is different from every other correctional facility (e.g., physical plant structure/age, geographic differences, equipment standards, staffing patterns, policies and procedures, etc.), each facility's administrative staff would determine the threshold for assigning an alert and subsequent color-code to the alert. This potential threshold is determined in accordance with the embodiments of the present invention. The risk number for Inmate 1 can be displayed in green, for example, and the risk number for Inmate 2 can be displayed in red, for example.

Once a risk number and, in some embodiments, a related color are assigned to a particular inmate, this information is openly displayed within any particular system chosen by a corrections facility or other agency. Typically a red color may be associated with risk numbers that are high and a green color may be associated with risk numbers that are low. However, embodiments of the present invention may utilize various colors to indicate high and low risk numbers. The colored number displays can be integrated into paper charts, electronic systems for automatic display and handheld devices depending upon the sophistication of the facility system(s). The data generated can be reported in various formats depending upon the need of the and facility—to include chronologic reports, unit reports, overall agency reports, etc. In some embodiments of the present invention, the reports can be blended into a standardized format and platform. These reports can give an overall picture of trends and problematic corrections facilities compared to those who perform better at protecting inmates from rape and exploitation.

Embodiments of the present invention may be utilized in virtually any corrections setting or facility, as typically all inmates are required to the evaluated for potential victimization. Embodiments of the present invention can be used by screening experts (corrections, medical, designees) in order to evaluate potential risks and plan for protective actions such as location disposition, added security, etc.

Embodiments of the present invention are capable of interacting with other software/systems in correctional facilities. For example, embodiments of the present invention may be configured to interact with systems and methods described in U.S. Pat. No. 8,441,353, which is incorporated herein by reference in its entirety, to automatically warn caregivers of potential dangers and using a "keep separate" modality to automatically segregate potential rapists from potential victims.

Figure 8:
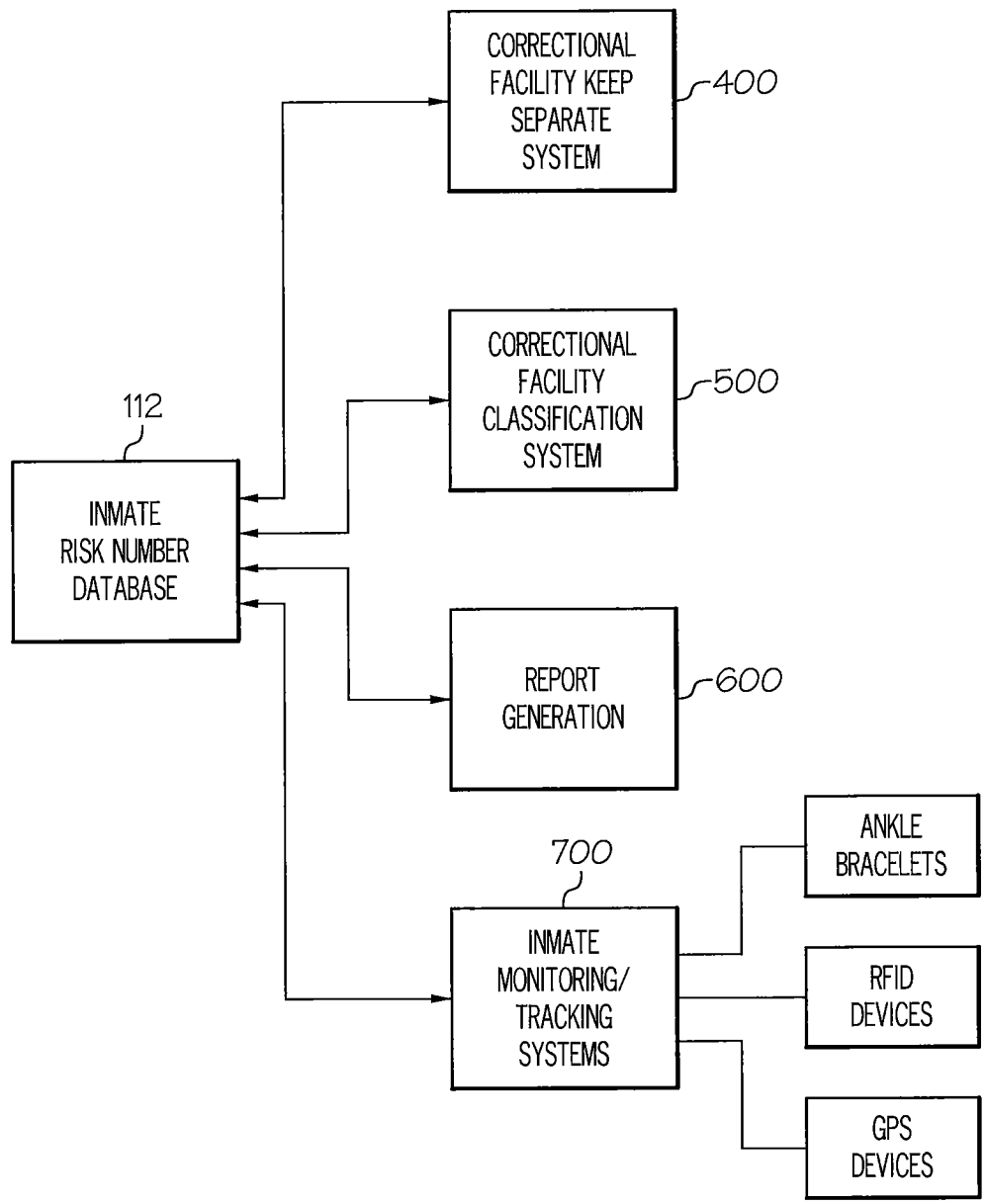
FIG. 8 is a block diagram that illustrates various systems/functions that can utilize information regarding prison inmates who may be vulnerable to rape and prison inmates who may be sexual predators, according to some embodiments of the present invention.

Referring to FIG. 8, various systems and functions can utilize the risk number assigned to inmates in a facility. For example, the inmate risk number database 112 may be in communication with a correctional facility "keep separate" system 400, a correctional facility classification system 500, and an inmate monitoring/tracking system 700. In addition, correctional facilities are required to prepare various reports indicating compliance with PREA. As such, a report generation function 600 of a facility can access the inmate risk number database 112 for the purpose of generating reports as required. Embodiments of the present invention are configured to generate internal as well as overarching external reports regarding data, trends and related metrics for personnel management, planning and budgeting.

Figure 9:
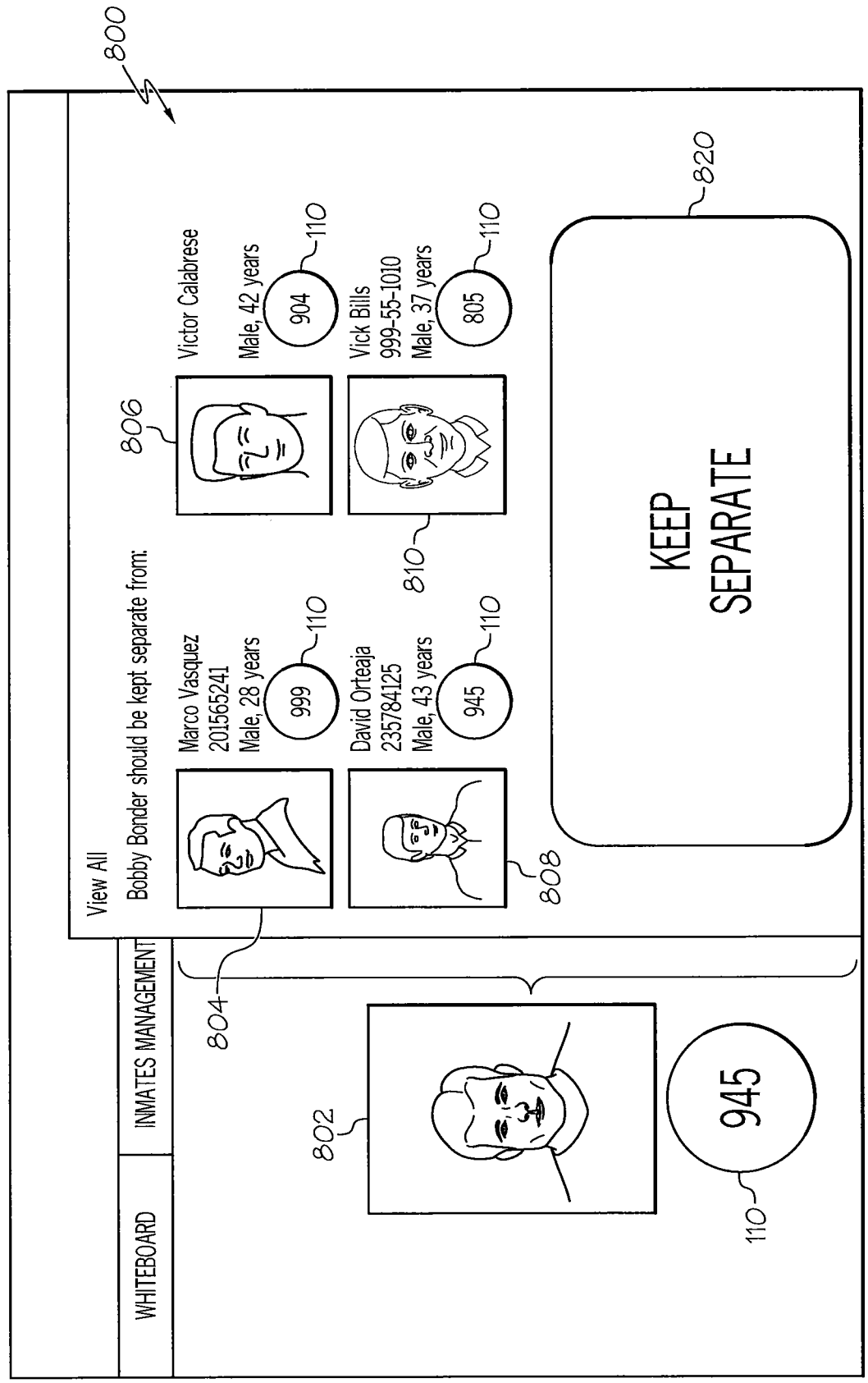
FIG. 9 is a GUI of a facility system that identifies inmates that may be potential abusers of another inmate, according to some embodiments of the present invention.

Referring to FIG. 9, a GUI 800 associated with a facility's "keep separate" system is illustrated. A particular inmate 802 has a risk number 110 that has a value of 945, which indicates the inmate 802 may be a potential victim. The GUI 800 also displays a listing of other inmates who are potential abusers and who should be kept separate from inmate 802. For example, inmate 804 has a risk number 110 with a value of 999, inmate 806 has a risk number 110 with a value of 904, inmate 808 has a risk number 110 with a value of 945, and inmate 810 has a risk number 110 with a value of 805. The illustrated GUI 800 displays a warning 820 to keep inmate 802 separate from inmates 804, 806, 808, and 810 in the facility. This may be communicated to alarm systems, RFID tag systems, door lock systems, etc., within a facility. For example, if inmate 802 is detected to be in a vicinity of inmate 804, an alarm system can be activated to notify facility officials. In addition, in some embodiments, doors or other barriers can be activated to physically isolate inmate 802 from inmate 804 when detected in a common area.

Figure 10:
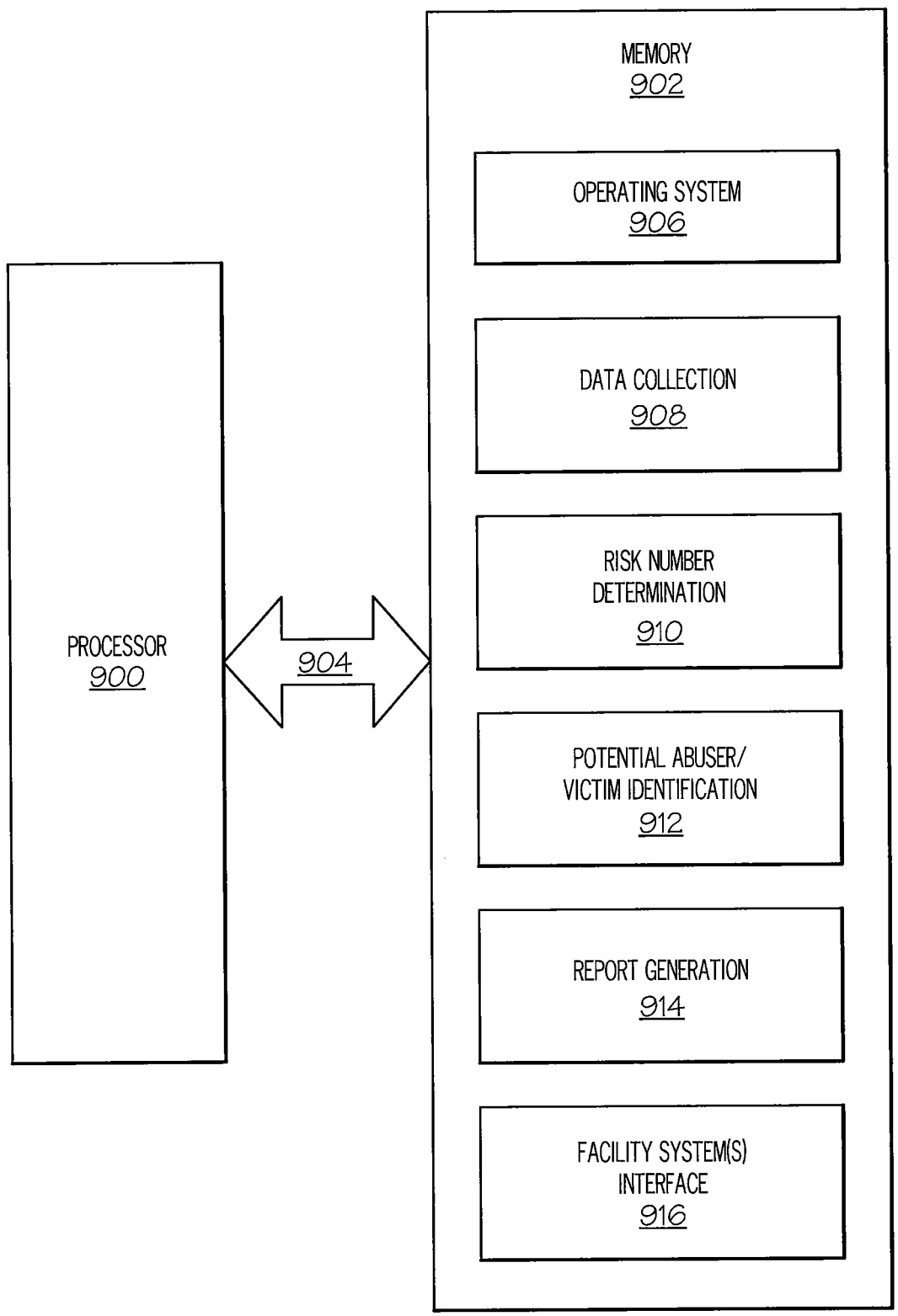
FIG. 10 is a block diagram that illustrates details of an exemplary processor and memory that may be used for predicting prison inmates who may be vulnerable to rape, and prison inmates who may be sexual predators, in accordance with embodiments of the present invention.

FIG. 10 illustrates an exemplary processor 900 and memory 902 that may be utilized in implementing various embodiments of the present invention. However, embodiments of the present invention are not limited to a single processor and memory. Multiple processors and/or memory may be utilized, as would be understood by those skilled in the art.

The processor 900 and memory 902 may be utilized in conjunction with existing correction facility computer systems or may be utilized as a standalone system. The processor 900 communicates with the memory 902 via an address/data bus 904. The processor 900 may be, for example, a commercially available or custom microprocessor or similar data processing device. The memory 902 is representative of the overall hierarchy of memory devices containing the software and data used to perform the various operations described herein. The memory 902 may include, but is not limited to, the following types of devices: cache, ROM, PROM, EPROM, EEPROM, flash, SRAM, and DRAM.

As shown in FIG. 10, the memory 902 may hold various categories of software and data: an operating system 906, a data collection module 908, a risk number determination module 910, a potential abuser/victim identification module 912, a report generation module 914, and a facility system(s) interface module 916. The operating system 906 may manage the resources of one or more devices used to implement embodiments of the present invention and may coordinate execution of various programs (e.g., the data collection module 908, the risk number determination module 910, the potential abuser/victim identification module 912, the report generation module 914, the facility system(s) interface module 916 etc.) by the processor 900. The operating system 906 can be any operating system suitable for use with a data processing system, such as IBM®, OS/2®, AIX® or z/OS® operating systems, Microsoft® Windows® operating systems, Android®, Unix or Linux™, etc.

The data collection module 908 comprises logic for collecting objective/measurable information from an inmate (Block 10, FIG. 1), for collecting clinical information about an inmate (Block 20, FIG. 1), and for collecting subjective information about an inmate (Block 30, FIG. 1). The risk number determination module 210 comprises logic for processing the objective, clinical, and subjective information to derive a risk number for an inmate (Block 40, FIG. 1). The potential abuser/victim identification module 912 comprises logic for identifying inmates in a facility that may be potential victims of sexual assault and for identifying inmates within the facility that may be potential sexual predators/abusers. The report generation module 914 comprises logic for preparing various reports needed to comply with PREA. The facility system(s) interface module 916 comprises logic for interfacing with various facility systems that can assist in physically separating potential victims from potential abusers.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A method of reducing the risk of sexual assault in a facility, the method comprising:
receiving objective information about a person housed in the facility from a first source;
receiving clinical information about the person from a second source;
obtaining subjective information about the person comprising observing the person and/or asking the person one or more predetermined questions;
converting the objective, clinical and subjective information into respective groups of one or more variables that can be processed by an algorithm;
processing the respective groups of one or more variables via the algorithm to derive a risk number for the person, wherein the risk number represents a risk of the person being vulnerable to rape within the facility or a risk of the person being a sexual predator within the facility;
identifying one or more other persons within the facility that may be a potential sexual victim of the person and/or that may be a potential sexual abuser of the person based upon the risk number of the person and respective risk numbers of each of the one or more other persons; and
activating one or more devices within the facility to facilitate isolation of the person from the one or more other persons that may be a potential sexual victim of the person and/or that may be a potential sexual abuser of the person responsive to detecting that the person is within a predetermined distance of the one or more other persons,
wherein activating one or more devices within the facility to facilitate isolation of the person comprises automatically locking one or more doors or barriers within the facility.

2. The method of claim 1, wherein the first source comprises one or more law enforcement databases, one or more court system databases, and/or one or more government databases, wherein the second source comprises one or more healthcare provider databases, and wherein receiving clinical information about the person from the second source comprises receiving physical information, psychiatric information, and/or medical information.

3. The method of claim 1, wherein converting the objective, clinical and subjective information into respective groups of one or more variables further comprises assigning a weighted coefficient to selected ones of the one or more variables in the respective groups.

4. The method of claim 1, wherein the facility is a correctional facility and the person is an inmate in the facility, and wherein receiving objective information about the person from a first source comprises receiving information about one or more of the following:
age, race, marital status, number of previous incarcerations of the person, violent nature of charges against the person, previous convictions of the person for sex related crimes against a child or adult, whether the person is incarcerated strictly for immigration purposes, convictions of the person for physically aggressive sexual act(s), prior convictions of the person for other violent offenses, history of institutional violence and/or sexual offence(s) by the person, and gang affiliation.

5. The method of claim 1, further comprising communicating an identification of the one or more other persons that may be a potential sexual victim of the person and/or that may be a potential sexual abuser of the person to a monitoring system of the facility.

6. The method of claim 1, wherein the one or more devices further comprise one or more electronic monitoring devices, one or more RFID devices, and/or one or more GPS devices.

7. The method of claim 1, further comprising communicating the risk number of the person to a monitoring system of the facility.

8. The method of claim 1, further comprising assigning a color code to the risk number of the person, wherein the color code represents a risk of the person being vulnerable to rape or a risk of the person being a sexual predator.

9. The method of claim 1, wherein the facility is a correctional facility and the person is an inmate in the facility.

10. The method of claim 1, wherein activating the one or more devices within the facility to facilitate isolation of the person from the one or more other persons is performed responsive to a determination that the risk number for the person exceeds a predetermined threshold.

11. The method of claim 1, wherein automatically locking one or more doors or barriers within the facility is performed by an automated door lock system.

12. A system for reducing the risk of sexual assault in a facility, the system comprising:
a data collection and storage component configured to receive objective information about a respective person housed within the facility from a first source, receive clinical information about the person from a second source, and receive subjective information about the person from an observer of the person; and at least one processor configured to:
convert the objective, clinical and subjective information into respective groups of one or more variables;
process the respective groups of one or more variables via at least one algorithm to derive a risk number for the person, wherein the risk number represents a risk of the person being vulnerable to rape within the facility or a risk of the person being a sexual predator within the facility;
assign a color code to the risk number of the person, wherein the color code represents a risk of the person being vulnerable to rape within the facility or a risk of the person being a sexual predator within the facility;
associate the color code and/or the risk number with the person within the data collection and storage component;
identify one or more other persons within the facility that may be a potential sexual victim of the person and/or that may be a potential sexual abuser of the person based upon the risk number of the person and respective risk numbers of each of the one or more other persons; and
transmit instructions to activate one or more devices within the facility to automatically provide physical isolation of the person from the one or more other persons that may be a potential sexual victim of the person and/or that may be a potential sexual abuser of the person responsive to detecting that the person is within a predetermined distance of the one or more other persons.

13. The system of claim 12, wherein the first source comprises one or more law enforcement databases, one or more court system databases, and/or one or more government databases, wherein the second source comprises one or more healthcare provider databases, and wherein the clinical information about the person comprises physical information, psychiatric information, and/or medical information.

14. The system of claim 12, wherein the at least one processor is configured to assign a weighted coefficient to selected ones of the one or more variables in the respective groups prior to processing the respective groups of one or more variables via the at least one algorithm to derive the risk number for the person.

15. The system of claim 12, wherein the facility is a correctional facility and the person is an inmate in the facility, and wherein the objective information about the person comprises one or more of the following: age, race, marital status, number of previous incarcerations of the person, violent nature of charges against the person, previous convictions of the person for sex related crimes against a child or adult, whether the person is incarcerated strictly for immigration purposes, convictions of the person for physically aggressive sexual
act(s), prior convictions of the person for other violent offenses, history of institutional violence and/or sexual offence(s) by the person, and gang affiliation.

16. The system of claim 12, wherein the at least one processor is configured to identify one or more other persons within the facility that may be a potential sexual victim of the person and/or that may be a potential sexual abuser of the person based upon the risk number of the person and respective risk numbers of each of the one or more other persons.

17. The system of claim 16, wherein the at least one processor is configured to communicate an identification of the one or more other persons that may be a potential sexual victim of the person and/or that may be a potential sexual abuser of the person to a monitoring system of the facility.

18. The system of claim 16, wherein the at least one processor is configured to activate one or more devices within the facility to facilitate isolation of the person from the one or more other persons that may be a potential sexual victim of the person and/or that may be a potential sexual abuser of the person.

19. The system of claim 18, wherein the one or more devices comprise one or more electronic monitoring devices, one or more RFID devices, and/or one or more GPS devices.

20. The system of claim 18, wherein the at least one processor is configured to a lock on one or more doors or barriers within the facility.

21. The system of claim 12, wherein the at least one processor is configured to communicate the risk number of the person to a monitoring system of the facility.

22. The system of claim 12, wherein the facility is a correctional facility and the person is an inmate in the facility.

23. A computer program product, comprising a non-transitory computer readable storage medium having encoded thereon instructions that, when executed on a processor, cause the processor to perform operations comprising:
receiving objective information about a person housed in a facility from a first source; receiving clinical information about the person from a second source;
receiving subjective information about the person from an observer of the person;
converting the objective, clinical and subjective information into respective groups of one or more variables that can be processed by an algorithm;
processing the respective groups of one or more variables via the algorithm to derive a risk number for the person, wherein the risk number represents a risk of the person being
vulnerable to rape within the facility or a risk of the person being a sexual predator within the facility;
identifying one or more other persons within the facility that may be a potential sexual victim of the person and/or that may be a potential sexual abuser of the person based upon the risk number of the person and respective risk numbers of each of the one or more other persons; and
activating one or more devices within the facility to automatically provide physical isolation of the person from the one or more other persons that may be a potential sexual victim of the person and/or that may be a potential sexual abuser of the person responsive to detecting that the person is within a predetermined distance of the one or more other persons.

24. The computer program product of claim 23, wherein the computer readable storage medium has encoded thereon instructions that, when executed on the processor, cause the processor to perform operations comprising:
communicating an identification of the one or more other persons that may be a potential sexual victim of the person and/or that may be a potential sexual abuser of the person to a monitoring system of the facility.

25. The computer program product of claim 23, wherein the computer readable storage medium has encoded thereon instructions that, when executed on the processor, cause the processor to perform operations comprising communicating the risk number of the person to a monitoring system of the facility.

26. The computer program product of claim 23, wherein activating the one or more devices within the facility to facilitate isolation of the person from the one or more other persons is performed responsive to a determination that the risk number for the person exceeds a predetermined threshold.

27. The computer program product of claim 23, wherein activating one or more devices within the facility to automatically provide physical isolation of the person comprises automatically locking one or more doors or barriers within the facility.

* * * * *